United States Patent
Dixon et al.

(10) Patent No.: US 9,682,047 B2
(45) Date of Patent: Jun. 20, 2017

(54) AUGMENTATION OF ONCOLOGY IMMUNOTHERAPIES BY PTEROSTILBENE CONTAINING COMPOSITIONS

(71) Applicant: THERAPEUTIC SOLUTIONS INTERNATIONAL, INC., Oceanside, CA (US)

(72) Inventors: Timothy G. Dixon, Oceanside, CA (US); Gerry B. Berg, Oceanside, CA (US); Robert F. Graham, Oceanside, CA (US); Santosh Kesari, Oceanside, CA (US); Thomas Ichim, San Diego, CA (US)

(73) Assignee: Therapeutic Solutions International, Inc., Oceanside, CA (US)

( * ) Notice: Subject to any disclaimer, the term of this patent is extended or adjusted under 35 U.S.C. 154(b) by 0 days.

(21) Appl. No.: 15/204,560

(22) Filed: Jul. 7, 2016

(65) Prior Publication Data

US 2016/0324801 A1 Nov. 10, 2016

Related U.S. Application Data

(60) Provisional application No. 62/190,170, filed on Jul. 8, 2015.

(51) Int. Cl.
| | | |
|---|---|---|
| *A61K 9/00* | (2006.01) | |
| *A61K 31/09* | (2006.01) | |
| *A61K 45/06* | (2006.01) | |
| *A61K 9/127* | (2006.01) | |
| *A61K 31/12* | (2006.01) | |
| *A61K 38/44* | (2006.01) | |
| *A61K 31/133* | (2006.01) | |
| *A61K 31/4525* | (2006.01) | |
| *A61K 31/385* | (2006.01) | |
| *A61K 38/20* | (2006.01) | |
| *A61K 9/14* | (2006.01) | |
| *A61K 9/48* | (2006.01) | |

(52) U.S. Cl.
CPC .............. *A61K 31/09* (2013.01); *A61K 9/127* (2013.01); *A61K 9/146* (2013.01); *A61K 9/4866* (2013.01); *A61K 31/12* (2013.01); *A61K 31/133* (2013.01); *A61K 31/385* (2013.01); *A61K 31/4525* (2013.01); *A61K 38/2013* (2013.01); *A61K 38/446* (2013.01); *A61K 45/06* (2013.01); *C12Y 115/01001* (2013.01)

(58) Field of Classification Search
None
See application file for complete search history.

(56) References Cited

U.S. PATENT DOCUMENTS

| | | | | |
|---|---|---|---|---|
| 8,227,510 B2* | 7/2012 | Estrela Ariquel | ...... | A61K 31/09 514/456 |
| 8,426,369 B2* | 4/2013 | Rimando | ............. | A61K 36/185 514/23 |
| 2010/0330078 A1* | 12/2010 | Bender | ............. | C07K 16/2842 424/133.1 |
| 2012/0088829 A1* | 4/2012 | Berl | ..................... | A61K 31/216 514/548 |
| 2013/0058873 A1* | 3/2013 | Jefferies | ................. | A61K 38/40 424/9.34 |
| 2013/0296440 A1* | 11/2013 | Bartos | .................... | A61K 31/12 514/679 |
| 2014/0141082 A1* | 5/2014 | Gao | ........................ | A61K 31/05 424/474 |
| 2014/0199296 A1* | 7/2014 | Bannister | ........... | A61K 31/7068 424/133.1 |
| 2014/0371271 A1* | 12/2014 | Park | ..................... | C07D 317/62 514/330 |
| 2015/0291609 A1* | 10/2015 | Wang | .................... | A61K 31/55 514/218 |

FOREIGN PATENT DOCUMENTS

WO 2014/075788 * 5/2014

OTHER PUBLICATIONS

Yang et al PLOS One col. 8 p. e62652 (May 2013).*
Schneider et al Gastroenterology, (May 2009) vol. 136, No. 5, Suppl. 1, pp. A936. Meeting Info.: Digestive Disease Week/110th Annual Meeting of the American-Gastroenterological-Association. Chicago, IL, USA. May 30-Jun. 4, 2009 (abstract only).*
Pan et al PLOS One vol. 9 p. e104459 (Aug. 2014).*
Mannal et al American Journal of Surgery vol. 200 p. 577 (2010).*
Li et al PLOS One vol. 8 p. e57542 (Mar. 2013).*
Fulda et al Drug Discovery Today vol. 15 p. 757 (2010).*
Almand, B., et al., Increased production of immature myeloid cells in cancer patients: a mechanism of immunosuppression in cancer. J Immunol, 2001. 166(1): p. 678-89.
Angelopoulou, K., et al., p53 gene mutation, tumor p53 protein overexpression, and serum p53 autoantibody generation in patients with breast cancer. Clin Biochem, 2000. 33(1): p. 53-62.
Ayari, C., et al., Bladder tumor infiltrating mature dendritic cells and macrophages as predictors of response to bacillus Calmette-Guerin immunotherapy. Eur Urol, 2009. 55(6): p. 1386-95.
Ayari, C., et al., High level of mature tumor-infiltrating dendritic cells predicts progression to muscle invasion in bladder cancer. Hum Pathol, 2013. 44(8): p. 1630-7.

(Continued)

*Primary Examiner* — Sheela J Huff
(74) *Attorney, Agent, or Firm* — Knobbe Martens Olson & Bear LLP

(57) ABSTRACT

Compositions and methods useful to enhancing, improving, or eliciting anti-tumor immune responses are disclosed. A pterostilbene containing composition is administered to a cancer patient at a sufficient concentration and frequency to induce de-repression of tumor targeting immune responses. The composition enhances antibody dependent cellular toxicity (ADCC) and augments efficacy of antigen specific immunotherapeutics such as trastuzumab and other monoclonal antibody therapies useful for treating cancer.

8 Claims, 2 Drawing Sheets

(56) References Cited

OTHER PUBLICATIONS

Barreiro, E., et al., Oxidative stress and inflammation in the normal airways and blood of patients with lung cancer and COPD. Free Radic Biol Med, 2013. 65: p. 859-71.
Bavaresco, L., et al., "Stilbene compounds: from the grapevine to wine." Drugs Exp Clin Res, 1999. 25(2-3): p. 57-63.
Beck, C., H. Schreiber, and D. Rowley, Role of TGF-beta in immune-evasion of cancer. Microsc Res Tech, 2001. 52(4): p. 387-95.
Bhaumik, S. and A. Khar, Induction of nitric oxide production by the peritoneal macrophages after intraperitoneal or subcutaneous transplantation of AK-5 tumor. Nitric Oxide, 1998. 2(6): p. 467-74.
Billingsley, K.G., et al., Macrophage-derived tumor necrosis factor and tumor-derived of leukemia inhibitory factor and interleukin-6: possible cellular mechanisms of cancer cachexia. Ann Surg Oncol, 1996. 3(1): p. 29-35.
Bjelakovic, G. and C. Gluud, Surviving antioxidant supplements. J Natl Cancer Inst, 2007. 99(10): p. 742-3.
Blackwell, K., et al., Plasma D-dimer levels in operable breast cancer patients correlate with clinical stage and axillary lymph node status. J Clin Oncol, 2000. 18(3): p. 600-8.
Bonta, I.L. and S. Ben-Efraim, Involvement of inflammatory mediators in macrophage antitumor activity. J Leukoc Biol, 1993. 54(6): p. 613-26.
Campbell, J.D., et al., Suppression of IL-2-induced T cell proliferation and phosphorylation of STAT3 and STAT5 by tumor-derived TGF beta is reversed by IL-15. J Immunol, 2001. 167(1): p. 553-61.
Chen, X., et al., Impaired expression of the CD3-zeta chain in peripheral blood T cells of patients with chronic myeloid leukaemia results in an increased susceptibility to apoptosis. Br J Haematol, 2000. 111(3): p. 817-25.
Cobanoglu, U., et al., Lipid peroxidation, DNA damage and coenzyme Q10 in lung cancer patients—markers for risk assessment? Asian Pac J Cancer Prev, 2011. 12(6): p. 1399-403.
Cochet, A., et al., Baseline diastolic dysfunction as a predictive factor of trastuzumab-mediated cardiotoxicity after adjuvant anthracycline therapy in breast cancer. Breast Cancer Res Treat, 2011. 130(3): p. 845-54.
Datta, J., et al., Rationale for a Multimodality Strategy to Enhance the Efficacy of Dendritic Cell-Based Cancer Immunotherapy. Front Immunol, 2015. 6: p. 271.
Didziapetriene, J., et al., Significance of blood serum catalase activity and malondialdehyde level for survival prognosis of ovarian cancer patients. Medicina (Kaunas), 2014. 50(4): p. 204-8.
Diepolder, H. and R. Obst, Making antigen invisible: a coinhibitory molecule regulates the interaction between T cells and dendritic cells. Expert Rev Vaccines, 2010. 9(3): p. 243-7.
Disis, M.L., et al., Generation of T-cell immunity to the HER-2/neu protein after active immunization with HER-2/neu peptide-based vaccines. J Clin Oncol, 2002. 20(11): p. 2624-32.
Disis, M.L., et al., Generation of immunity to the HER-2/neu oncogenic protein in patients with breast and ovarian cancer using a peptide-based vaccine. Clin Cancer Res, 1999. 5(6): p. 1289-97.
Dix, A.R., et al., Immune defects observed in patients with primary malignant brain tumors. J Neuroimmunol, 1999. 100(1-2): p. 216-32.
El Zarrad, M.K., et al., Trastuzumab alters the expression of genes essential for cardiac function and induces ultrastructural changes of cardiomyocytes in mice. PLoS One, 2013. 8(11): p. e79543.
Farolfi, A., et al., "Trastuzumab-induced cardiotoxicity in early breast cancer patients: a retrospective study of possible risk and protective factors." Heart, 2013. 99(9): p. 634-9.
Fearon, K.C., et al., Pancreatic cancer as a model: inflammatory mediators, acute-phase response, and cancer cachexia. World J Surg, 1999. 23(6): p. 584-8.
Ferrigno, D., G. Buccheri, and I. Ricca, Prognostic significance of blood coagulation tests in lung cancer. Eur Respir J, 2001. 17(4): p. 667-73.
Fife, B.T., et al., Interactions between PD-1 and PD-L1 promote tolerance by blocking the TCR-induced stop signal. Nat Immunol, 2009. 10(11): p. 1185-92.
Fischer, J.R., et al., Decrease of interleukin-2 secretion is a new independent prognostic factor associated with poor survival in patients with small-cell lung cancer. Ann Oncol, 1997. 8(5): p. 457-61.
Gajewski, T.F. et al., "Innate and adaptive immune cells in the tumor microenvironment." Nat Immunol, 2013. 14(10): p. 1014-22.
Gastman, B.R., et al., Tumor-induced apoptosis of T lymphocytes: elucidation of intracellular apoptotic events. Blood, 2000. 95(6): p. 2015-23.
Gluckman, J.C., et al., In vitro generation of human dendritic cells and cell therapy. Cytokines Cell Mol Ther, 1997. 3(3): p. 187-96.
Goydos, J.S., et al., A phase I trial of a synthetic mucin peptide vaccine. Induction of specific immune reactivity in patients with adenocarcinoma. J Surg Res, 1996. 63(1): p. 298-304.
Gupta, R.K., et al., Interactions between oxidative stress, lipid profile and antioxidants in breast cancer: a case control study. Asian Pac J Cancer Prev, 2012. 13(12): p. 6295-8.
Guzel, S., et al., Association of Pb, Cd, and Se concentrations and oxidative damage-related markers in different grades of prostate carcinoma. Biol Trace Elem Res, 2012. 145(1): p. 23-32.
Healy, C.G., et al., Impaired expression and function of signal-transducing zeta chains in peripheral T cells and natural killer cells in patients with prostate cancer. Cytometry, 1998. 32(2): p. 109-19.
Herrera, A.C., et al., Impact of tumor removal on the systemic oxidative profile of patients with breast cancer discloses lipid peroxidation at diagnosis as a putative marker of disease recurrence. Clin Breast Cancer, 2014. 14(6): p. 451-9.
Horiguchi, S., et al., Primary chemically induced tumors induce profound immunosuppression concomitant with apoptosis and alterations in signal transduction in T cells and NK cells. Cancer Res, 1999. 59(12): p. 2950-6.
Hu, M., et al., Decreased intratumoral Foxp3 Tregs and increased dendritic cell density by neoadjuvant chemotherapy associated with favorable prognosis in advanced gastric cancer. Int J Clin Exp Pathol, 2014. 7(8): p. 4685-94.
Huo, W., et al., Antioxidant enzyme levels in pathogenesis of oral squamous cell carcinoma (OSCC). Drug Res (Stuttg), 2014. 64(11): p. 629-32.
Ishigami, S., et al., CD3-zetachain expression of intratumoral lymphocytes is closely related to survival in gastric carcinoma patients. Cancer, 2002. 94(5): p. 1437-42.
Ishihara, K. and T. Hirano, IL-6 in autoimmune disease and chronic inflammatory proliferative disease. Cytokine Growth Factor Rev, 2002. 13(4-5): p. 357.
Jager, D., et al., Identification of tumor antigens as potential target antigens for immunotherapy by serological expression cloning. Cancer Immunol Immunother, 2004. 53(3): p. 144-7.
Joseph, J.A., et al., "Cellular and behavioral effects of stilbene resveratrol analogues: implications for reducing the deleterious effects of aging." J Agric Food Chem, 2008. 56(22): p. 10544-51.
Kallio, J.P., et al., Soluble immunological parameters and early prognosis of renal cell cancer patients. J Exp Clin Cancer Res, 2001. 20(4): p. 523-8.
Kamate, C., et al., Inflammation and cancer, the mastocytoma P815 tumor model revisited: triggering of macrophage activation in vitro with pro-tumorigenic consequences. Int J Cancer, 2002. 1000(5): p. 571-9.
Karki, K., et al., Expression of serum toll-like receptor 9 and oxidative damage markers in benign and malignant breast diseases. DNA Cell Biol, 2014. 33(9): p. 630-6.
Karimi, N. and V.D. Roshan, Change in adiponectin and oxidative stress after modifiable lifestyle interventions in breast cancer cases. Asian Pac J Cancer Prev, 2013. 14(5): p. 2845-50.
Kiessling, R., et al., Tumor-induced immune dysfunction. Cancer Immunol Immunother, 1999. 48(7): p. 353-62.
Kim, C.W., et al., Alteration of signal-transducing molecules and phenotypical characteristics in peripheral blood lymphocytes from gastric carcinoma patients. Pathobiology, 1999. 67(3): p. 123-8.
Kim, H.J., J.K. Park, and Y.G. Kim, Suppression of NF-kappaB activation in normal T cells by supernatant fluid from human renal cell carcinomas. J Korean Med Sci, 1999. 14(3): p. 299-303.

(56) References Cited

OTHER PUBLICATIONS

Ko, B.K., et al., Clinical studies of vaccines targeting breast cancer. Clin Cancer Res, 2003. 9(9): p. 3222-34.

Kono, K., et al., Hydrogen peroxide secreted by tumor-derived macrophages down-modulates signal-transducing zeta molecules and inhibits tumor-specific T cell-and natural killer cell-mediated cytotoxicity. Eur J Immunol, 1996. 26(6): p. 1308-13.

Korde, S.D., et al., Enhanced nitrosative and oxidative stress with decreased total antioxidant capacity in patients with oral precancer and oral squamous cell carcinoma. Oncology, 2011. 80(5-6): p. 382-9.

Laytragoon-Lewin, N., et al., Alteration of cellular mediated cytotoxicity, T cell receptor zeta (TcR zeta) and apoptosis related gene expression in nasopharyngeal carcinoma (NPC) patients: possible clinical relevance. Anticancer Res, 2000. 20(2B): p. 1093-100.

Leek, R.D., et al., Association of macrophage infiltration with angiogenesis and prognosis in invasive breast carcinoma. Cancer Res, 1996. 56(20): p. 4625-9.

Lewis, J.G. and D.O. Adams, Inflammation, oxidative DNA damage, and carcinogenesis. Environ Health Perspect, 1987. 76: p. 19-27.

Lewis, J.S., et al., Expression of vascular endothelial growth factor by macrophages is up-regulated in poorly vascularized areas of breast carcinomas. J Pathol, 2000. 192(2): p. 150-8.

Li, T., et al., Glutathione S-transferase P1 correlated with oxidative stress in hepatocellular carcinoma. Int J Med Sci, 2013. 10(6): p. 683-90.

Liska, V., et al., Infiltration of colorectal carcinoma by S100+ dendritic cells and CD57+ lymphocytes as independent prognostic factors after radical surgical treatment. Anticancer Res, 2012. 32(5): p. 2129-32.

Ljungberg, B., K. Grankvist, and T. Rasmuson, Serum interleukin-6 in relation to acute-phase reactants and survival in patients with renal cell carcinoma. Eur J Cancer, 1997. 33(11): p. 1794-8.

Ma, Y., et al., Relation between gastric cancer and protein oxidation, DNA damage, and lipid peroxidation. Oxid Med Cell Longev, 2013. 2013: p. 543760.

Mahmoud, F.A. and N.I. Rivera, The role of C-reactive protein as a prognostic indicator in advanced cancer. Curr Oncol Rep, 2002. 4(3): p. 250-5.

Makitie, T., et al., Tumor-infiltrating macrophages (CD68(+) cells) and prognosis in malignant uveal melanoma. Invest Ophthalmol Vis Sci, 2001. 42(7): p. 1414-21.

Marakala, V., M. Malathi, and A.R. Shivashankara, Lipid peroxidation and antioxidant vitamin status in oral cavity and oropharyngeal cancer patients. Asian Pac J Cancer Prev, 2012. 13(11): p. 5763-5.

Marana, H.R., et al., Reduced immunologic cell performance as a prognostic parameter for advanced cervical cancer. Int J Gynecol Cancer, 2000. 10(1): p. 67-73.

Margaret, A.L., E. Syahruddin, and S.I. Wanandi, Low activity of manganese superoxide dismutase (MnSOD) in blood of lung cancer patients with smoking history: relationship to oxidative stress. Asian Pac J Cancer Prev, 2011. 12(11): p. 3049-53.

Martin-Cordero, C., et al., "Pro-oxidant natural products as anticancer agents." Curr Drug Targets, 2012. 13(8): p. 1006-28.

McCormack, D. and D. McFadden, "Pterostilbene and cancer: current review." J Surg Res, 2012. 173(2): p. e53-61.

McMillan, D.C., et al., Albumin concentrations are primarily determined by the body cell mass and the systemic inflammatory response in cancer patients with weight loss. Nutr Cancer, 2001. 39(2): p. 210-3.

Mehdi, W.A., J.A. Zainulabdeen, and A.A. Mehde, Investigation of the antioxidant status in multiple myeloma patients: effects of therapy. Asian Pac J Cancer Prev, 2013. 14(6): p. 3663-7.

Mizoguchi, H., et al., Alterations in signal transduction molecules in T lymphocytes from tumor-bearing mice. Science, 1992. 258(5089): p. 1795-8.

Moja, L., et al., Trastuzumab containing regimens for early breast cancer. Cochrane Database Syst Rev, 2012. 4: p. CD006243.

Murr, C., et al., Neopterin as a marker for immune system activation. Curr Drug Metab, 2002. 3(2): p. 175-87.

Musselli, C., et al., Reevaluation of the cellular immune response in breast cancer patients vaccinated with MUC1. Int J Cancer, 2002. 97(5): p. 660-7.

Nathan, F.M., et al., Oxidative stress and antioxidant status in primary bone and soft tissue sarcoma. BMC Cancer, 2011. 11: p. 382.

Ng, C.S., et al., Mechanisms of immune evasion by renal cell carcinoma: tumor-induced T-lymphocyte apoptosis and NFkappaB suppression. Urology, 2002. 59(1): p. 9-14.

Nourazarian, A.R., P. Kangari, and A. Salmaninejad, Roles of oxidative stress in the development and progression of breast cancer. Asian Pac J Cancer Prev, 2014. 15(12): p. 4745-51.

Nowicki, A., et al., Impaired tumor growth in colony-stimulating factor 1 (CSF-1)-deficient, macrophage-deficient op/op mouse: evidence for a role of CSF-1-dependent macrophages in formation of tumor stroma. Int J Cancer, 1996. 65(1): p. 112-9.

Oya, M., et al., High preoperative plasma D-dimer level is associated with advanced tumor stage and short survival after curative resection in patients with colorectal cancer. Jpn J Clin Oncol, 2001. 31(8): p. 388-94.

Pan, M.H., et al., "Pterostilbene inhibited tumor invasion via suppressing multiple signal transduction pathways in human hepatocellular carcinoma cells." Carcinogenesis, 2009. 30(7): p. 1234-42.

Pande, D., et al., Vascular endothelial growth factor levels in relation to oxidative damage and antioxidant status in patients with breast cancer. J Breast Cancer, 2011. 14(3): p. 181-4.

Park, E.S., et al., Pterostilbene, a natural dimethylated analog of resveratrol, inhibits rat aortic vascular smooth muscle cell proliferation by blocking Akt-dependent pathway. Vascul Pharmacol, 2010. 53(1-2): p. 61-7.

Paul, S., et al., "Dietary intake of pterostilbene, a constituent of blueberries, inhibits the beta-catenin/p65 downstream signaling pathway and colon carcinogenesis in rats." Carcinogenesis, 2010. 31(7): p. 1272-8.

Pirincci, N., et al., Serum prolidase activity, oxidative stress, and antioxidant enzyme levels in patients with renal cell carcinoma. Toxicol Ind Health, 2013.

Rimando, A.M. et al., "Biological/chemopreventive activity of stilbenes and their effect on colon cancer." Planta Med, 2008. 74(13): p. 1635-43.

Rimando, A.M., et al., "Cancer chemopreventive and antioxidant activities of pterostilbene, a naturally occurring analogue of resveratrol." J Agric Food Chem, 2002. 50(12): p. 3453-7.

Rimando, A.M., et al., "Pterostilbene, a new agonist for the peroxisome proliferator-activated receptor alpha-isoform, lowers plasma lipoproteins and cholesterol in hypercholesterolemic hamsters." J Agric Food Chem, 2005. 53(9): p. 3403-7.

Rosenberg, S.A., Immunotherapy and gene therapy of cancer. Cancer Res, 1991. 51(18 Suppl): p. 5074s-5079s.

Russo, G., et al., Role of renal function on the development of cardiotoxicity associated with trastuzumab-based adjuvant chemotherapy for early breast cancer. Intern Emerg Med, 2012. 7(5): p. 439-46.

Rutkowski, P., et al., Cytokine serum levels in soft tissue sarcoma patients: correlations with clinico-pathological features and prognosis. Int J Cancer, 2002. 100(4): p. 463-71.

Salzman, R., et al., High perioperative level of oxidative stress as a prognostic tool for identifying patients with a high risk of recurrence of head and neck squamous cell carcinoma. Int J Clin Oncol, 2010. 15(6): p. 565-70.

Sandmaier, B.M., et al., Evidence of a cellular immune response against sialyl-Tn in breast and ovarian cancer patients after high-dose chemotherapy, stem cell rescue, and immunization with Theratope STn-KLH cancer vaccine. J Immunother, 1999. 22(1): p. 54-66.

Satheesh, Amarnath M. and L. Pari, "The antioxidant role of pterostilbene in streptozotocin-nicotinamide-induced type 2 diabetes mellitus in Wistar rats." J Pharm Pharmacol, 2006. 58(11): p. 1483-90.

(56) References Cited

OTHER PUBLICATIONS

Schmielau, J. and O.J. Finn, Activated granulocytes and granulocyte-derived hydrogen peroxide are the underlying mechanism of suppression of t-cell function in advanced cancer patients. Cancer Res, 2001. 61(12): p. 4756-60.

Schwartz, R.N., L. Stover, and J. Dutcher, Managing toxicities of high-dose interleukin-2. Oncology (Williston Park), 2002. 16(11 Suppl 13): p. 11-20.

Scott, A.M., J.D. Wolchok, and L.J. Old, Antibody therapy of cancer. Nat Rev Cancer, 2012. 12(4): p. 278-87.

Seidman, A., et al., "Cardiac dysfunction in the trastuzumab clinical trials experience." J Clin Oncol, 2002. 20(5): p. 1215-21.

Smith, P.C., et al., Interleukin-6 and prostate cancer progression. Cytokine Growth Factor Rev, 2001. 12(1): p. 33-40.

Tabuchi, T., et al., Granulocyte apheresis as a possible new approach in cancer therapy: A pilot study involving two cases. Cancer Detect Prev, 1999. 23(5): p. 417-21.

Takahashi, A., et al., Elevated caspase-3 activity in peripheral blood T cells coexists with increased degree of T-cell apoptosis and down-regulation of TCR zeta molecules in patients with gastric cancer. Clin Cancer Res, 2001. 7(1): p. 74-80.

Taylor, D.D., et al., Modulation of TcR/CD3-zeta chain expression by a circulating factor derived from ovarian cancer patients. Br J Cancer, 2001. 84(12): p. 1624-9.

Tilkin, A.F., et al., Primary proliferative T cell response to wild-type p53 protein in patients with breast cancer. Eur J Immunol, 1995. 25(6): p. 1765-9.

Tsuboi, A., et al., Enhanced induction of human WT1-specific cytotoxic T lymphocytes with a 9-mer WT1 peptide modified at HLA-A*2402-binding residues. Cancer Immunol Immunother, 2002. 51(11-12): p. 614-20.

Ungefroren, H., et al., Immunological escape mechanisms in pancreatic carcinoma. Ann N Y Acad Sci, 1999. 880: p. 243-51.

Valkovic, T., et al., Correlation between vascular endothelial growth factor, angiogenesis, and tumor-associated macrophages in invasive ductal breast carcinoma. Virchows Arch, 2002. 440(6): p. 583-8.

Wang, B., et al., "Resveratrol preserves mitochondrial function, stimulates mitochondrial biogenesis, and attenuates oxidative stress in regulatory T cells of mice fed a high-fat diet." J Food Sci, 2014. 79(9): p. H1823-31.

Wang, C., et al., Lipid peroxidation and altered anti-oxidant status in breast adenocarcinoma patients. Drug Res (Stuttg), 2014. 64(12): p. 690-2.

Whisler, R.L., L.S. Gray, and K.V. Hackshaw, Rheumatology, a clinical overview. Clin Podiatr Med Surg, 2002. 19(1): p. 149-61, vii.

Woditschka, S., et al., DNA double-strand break repair genes and oxidative damage in brain metastasis of breast cancer. J Natl Cancer Inst, 2014. 106(7).

Yahya, R.S., et al., Role of interleukin-8 and oxidative stress in patients with hepatocellular carcinoma. Clin Lab, 2013. 59(9-10): p. 969-76.

Yamazaki, H., et al., Changes in natural killer cell activity by external radiotherapy and/or brachytherapy. Oncol Rep, 2002. 9(2): p. 359-63.

Yang, Y., et al., "Resveratrol induces the suppression of tumor-derived CD4+CD25+ regulatory T cells." Int Immunopharmacol, 2008. 8(4): p. 542-7.

Young, M.R., et al., Suppressor alveolar macrophages in mice bearing metastatic Lewis lung carcinoma tumors. J Leukoc Biol, 1987. 42(6): p. 682-8.

Zelen, I., et al., Antioxidant enzymes activities and plasma levels of oxidative stress markers in B-chronic lymphocytic leukemia patients. J BUON, 2010. 15(2): p. 330-6.

Zou, T. et al., "Resveratrol Inhibits CD4+ T cell activation by enhancing the expression and activity of Sirt1." PLoS One, 2013. 8(9): p. e75139.

* cited by examiner

AUGMENTATION OF ONCOLOGY IMMUNOTHERAPIES BY PTEROSTILBENE CONTAINING COMPOSITIONS

RELATED APPLICATIONS

The present application claims the benefit of priority to U.S. Provisional Patent Application No. 62/190,170, filed Jul. 8, 2015, the disclosure of which is incorporated by reference herein in its entirety.

FIELD OF THE DISCLOSURE

The disclosure relates generally to compositions and methods for treating cancer and improving responses to cancer drug therapies using a nutraceutical formulation containing pterostilbene.

BACKGROUND

Cancer is second only to cardiovascular disease as a cause of death in the United States. According to the American Cancer Society, there will be an estimated 1,658,210 new cancer cases diagnosed and 595,690 cancer deaths in the US in 2016. (The Agency for Healthcare research and Quality (AHRQ) estimates that the direct medical costs (total of all health care costs) for cancer in the US in 2011 were $88.7 billion.

Modalities useful in the treatment of cancer include chemotherapy, radiation therapy, surgery, immunotherapy, and other gene-, protein- or cell-based treatments. Conventional cancer therapies have many drawbacks including toxicity and significant side effects often limit the ability of patients to continue treatment, including immunosuppression, and damage to vital organs. Cancer cells eventually develop multi-drug resistance after being exposed to one or more anticancer agents. Most chemotherapeutic drugs act as anti-proliferative agents, targeting different stages of the cell cycle, thereby interfering with the function of healthy tissues and organs. Given the differing sensitivity of tumor cells to treatment, the ability of tumors to mutate and adapt to therapies, as well as the plethora of mechanisms that the tumor uses simultaneously in order to subvert host defenses, it is commonplace for multi-drug regimens to be used in cancer treatment. In turn, drug interactions and side effects that patients must contend with can increase exponentially.

Innumerable researchers and companies have searched for improvements in the treatments for the wide array of cancers. Companies are advancing bioactive agents including chemical entities, e.g., small molecules, and biologics, e.g., antibodies, with the desire of providing more beneficial therapies for cancer. Some bioactive agents have worked and provided beneficial therapeutic effects in some individuals or cancer types and others have failed or had minimal therapeutic effects or side effects that precluded completion of treatment due to organ toxicity, acute events such as thrombosis, and/or patient intolerance.

Analysis of the immunologic features of the tumor microenvironment is enabling rapid development of multiple new therapeutic strategies against various types of cancer as well as the identification of potential biomarkers for clinical benefit. Some cancers display hundreds or even thousands of mutations in coding exons, representing a large repertoire of antigens to serve as potential targets for the immune system. However, despite these abundant antigens, most cancers can evade immune mediated rejection, despite the ability to detect spontaneous anti-tumor immune responses in the majority of cancer patients (Gajewski, T. F., H. Schreiber, and Y. X. Fu, Innate and adaptive immune cells in the tumor microenvironment. Nat Immunol, 2013. 14(10): p. 1014-22), which is incorporated herein by reference in its entirety.

There is an emerging portfolio of inhibitory checkpoints that can influence the physiology of innate immune cells including dendritic cells, macrophages, natural killer (NK) cells, and T cells to harness their effector function in order to over-ride the tumor's inhibitor signals. A focal point of cancer therapeutics is therefore the discovery of novel therapeutic strategies of fine tuning and augmenting the appropriate anti-tumor responses. Moreover, it is known in the art that a synergistic combination of strategies directed toward overcoming the cancer's immune inhibitory signals and stimulating the endogenous anti-cancer immune response is believed to offer therapeutic advantages. Finding the right combinations of drugs to effectively treat a particular cancer, as well as limiting toxicity, have remained the two major thrusts in the art of clinical cancer research.

Different polyphenolic compounds of natural origin, such as trans-resveratrol (trans-3,5,4'-trihydroxystilbene, t-RESV), have been studied for their potential antitumor properties (3). Resveratrol (trans- or (E)-3,5,4'-trihydroxystilbene (1)) is a phytoalexin produced in plants and popularized as a beneficial ingredient of red wine. Resveratrol, its cis- or (Z)-isomer (2), and another stilbene derivative, pterostilbene (3), exhibit some anti-cancer activity. Cancer chemopreventive activity of t-RESV was first reported by Pan et al. (4). However, anticancer properties of t-RESV are limited due to the low systemic bioavailability of t-RESV (5). Thus, structural modifications of the t-RESV molecule appeared necessary in order to increase the bioavailability while preserving its biological activity. Resveratrol has also been produced by chemical synthesis and is sold as a nutritional supplement derived primarily from Japanese knotweed.

SUMMARY

The present disclosure is directed to compositions and methods for enhancing, improving, or eliciting anti-tumor immune responses in a subject. A pterostilbene containing composition is administered to a cancer patient at a sufficient concentration and frequency to induce de-repression of tumor targeting immune responses. The composition enhances antibody dependent cellular toxicity (ADCC) and augments efficacy of antigen specific immunotherapeutics such as trastuzumab and other monoclonal antibody therapies useful for treating cancer.

In some embodiments is provided a method of treating cancer in a subject having a tumor. In some embodiments, the method includes administering to the subject a composition having an effective amount of pterostilbene and an anti-cancer antibody.

In some embodiments, the effective amount of pterostilbene increases an immune response in the subject. In some embodiments, the effective amount of pterostilbene does not kill cancer cells. In some embodiments, an effective amount of pterostilbene increases an anti-tumor immune response in a subject. In some embodiments, the effective amount of pterostilbene does not kill tumor cells.

In some embodiments, an effective amount of pterostilbene includes an amount is an amount sufficient to cause an increase in an anti-tumor immune response in a subject. In some embodiments, an effective amount of pterostilbene is a daily dose of about 1, 2, 3, 4, 5, 6, 7, 8, 9, 10, 15, 20, 25, 30, 35, 40, 45, 50, 60, 70, 80, 90, 100, 110, 120, 130, 140, 150, 160, 170, 180, 190, 200, 250, 300, 350, 400, 450, 500, 600, 700, 800, 900, 1000, 1100, 1200, 1300, 1400, 1500, 1600, 1700, 1800, 1900, or 2000 mg, or a value within a range defined by any two of the aforementioned values.

In some embodiments, the anti-cancer antibody is selected from the group of rituximab, trastuzumab, nimotuzumab, alemtuzumab, gemtuzumab, ipilimumab, tremelimumab, nivolumab, pembrolizumab, and pidilizumab.

In some embodiments is provided a method of treating cancer in a subject. In some embodiments, the method includes administering a composition having an effective amount of pterostilbene to elicit an immune response in the subject. In some embodiments, eliciting an immune response in a subject includes increasing the ability of immune cells to inhibit cancer cell proliferation.

In some embodiments, eliciting an immune response in the subject is determined by assessing the function of immune cells. In some embodiments, the immune cells are selected from the group of B cells, T cells, innate lymphoid cells, natural killer cells, natural killer T cells, gamma delta T cells, macrophages, monocytes, dendritic cells, neutrophils, and myeloid derived suppressor cells.

In some embodiments, the immune cells include Th1 cells. In some embodiments, the Th1 cells are capable of secreting cytokines selected from the group of interferon gamma, interleukin 2, and TNF-beta. In some embodiments, the Th1 cells express markers that are selected from the group of CD4, CD94, CD119 (IFNγ R1), CD183 (CXCR3), CD186 (CXCR6), CD191 (CCR1), CD195 (CCR5), CD212 (IL-12Rβ1&2), CD254 (RANKL), CD278 (ICOS), IL-18R, MRP1, NOTCH3, and TIM3. Thus, in some embodiments, the method of treating cancer by administering pterostilbene relates to the production and quantification of secreted cytokines.

In some embodiments, the immune cells include Th2 cells. In some embodiments, the Th2 cells are capable of secreting cytokines selected from of the group of IL-4, IL-5, IL-6, IL-9, IL-10, and IL-13. In some embodiments, the Th2 cells express markers that are selected from the group of CRTH2, CCR4, and CCR3.

In some embodiments, the composition further includes a chemotherapeutic agent. In some embodiments, the chemotherapeutic agent is an anti-cancer antibody. In some embodiments, the anti-cancer antibody is selected from the group of rituximab, trastuzumab, nimotuzumab, alemtuzumab, gemtuzumab, ipilimumab, tremelimumab, nivolumab, pembrolizumab, and pidilizumab.

In some embodiments, pterostilbene is administered daily at a concentration of about 0.007 mg to about 1500 mg pterostilbene per kg metabolic weight. In some embodiments, pterostilbene is administered daily at a concentration of 0.007, 0.01, 0.02, 0.05, 0.1, 0.5, 1, 5, 10, 50, 100, 150, 200, 500, 1000, or 1500 mg of pterostilbene per kg of metabolic weight, or a value within a range defined by any two of the aforementioned values. In some embodiments, pterostilbene is administered in capsules at a dose of 10, 20, 30, 40, 50, 60, 70, 80, 90, 100, 110, 120, 130, 140, 150, 160, 170, 180, 190, 200, 250, 300, 400, or 500 mg at least twice daily, or a value within a range defined by any two of the aforementioned values. In some embodiments, pterostilbene is administered in capsules at a dose of 100 mg at least twice daily.

In some embodiments, the composition further includes one or more of superoxide dismutase, curcumin, dimethylaminoethanol (DMAE), alpha lipoic acid, and piperine.

In some embodiments is provided a composition for enhancing, improving, or eliciting anti-tumor immune responses in a cancer patient. In some embodiments, the composition includes pterostilbene. In some embodiments, the composition further includes one or more of superoxide dismutase, curcumin, alpha lipoic acid, piperine, 2-dimethylaminoethanol, and a pharmaceutically acceptable carrier. In some embodiments, pterostilbene is formulated as liposomal pterostilbene.

In some embodiments, the composition is contained in capsules. In some embodiments, the capsules each contain the following amounts, or a value defined within a range of any of the amounts described herein: 10, 20, 30, 40, 50, 60, 70, 80, 90, 100, 150, 200, 300, 400 or 500 mg pterostilbene; 10, 20, 30, 40, 50, 60, 70, 80, 90, 100, 150, 200, 300, 400 or 500 mg superoxide dismutase; 10, 20, 30, 40, 50, 60, 70, 80, 90, 100, 106, 150, 200, 300, 400 or 500 mg curcumin; 5, 10, 20, 30, 40, 50, 60, 70, 80, 90, 100, 150, 200, 300, 400 or 500 mg alpha lipoic acid, 0.1, 0.5, 1, 2, 3, 4, 5, 6, 7, 8, 9, 10, 15, 20, 30, 40 or 50 mg piperine; and 10, 20, 30, 40, 50, 60, 62, 70, 80, 90, 100, 150, 200, 300, 400 or 500 mg 2-dimethylaminoethanol. In some embodiments, the capsules each contain about 100 mg pterostilbene, 100 mg superoxide dismutase, 106 mg curcumin, 50 mg alpha lipoic acid, 5 mg piperine, and 62 mg 2-dimethylaminoethanol.

In some embodiments, the composition further includes a chemotherapeutic agent. In some embodiments, the chemotherapeutic agent is an anti-cancer antibody selected from the group of rituximab, trastuzumab, nimotuzumab, alemtuzumab, gemtuzumab, ipilimumab, tremelimumab, nivolumab, pembrolizumab, and pidilizumab.

DETAILED DESCRIPTION

Figure 1:
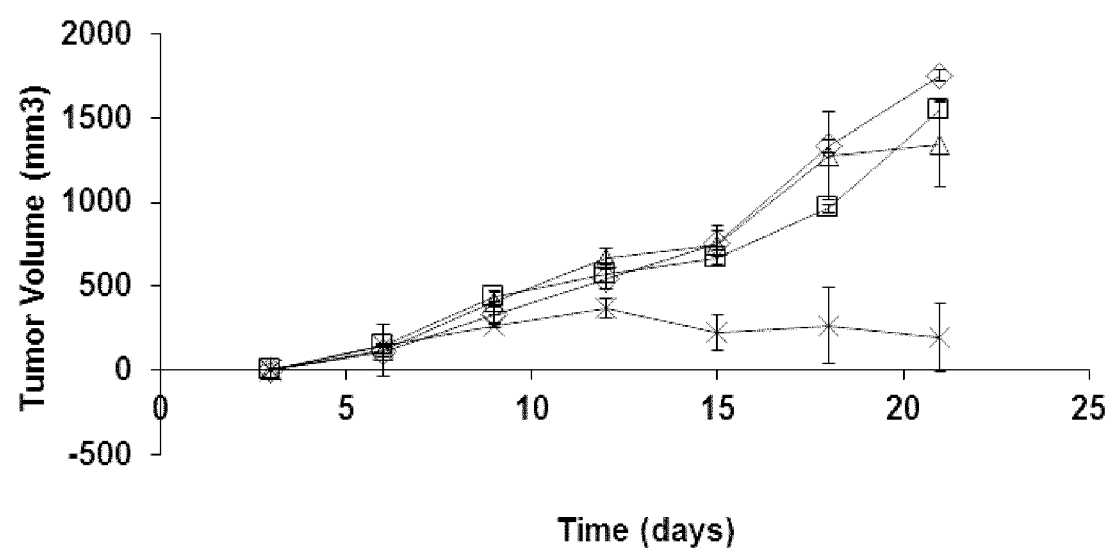
FIG. 1 illustrates the synergistic inhibition of B16 melanoma in mice when treated with the combination of IL-2 and pterostilbene. Mice were treated every second day with: saline (diamonds—◇); 25 μg/kg pterostilbene (squares—□); 500 IU/mouse IL-2 (triangles—Δ); and a combination of IL-2 and pterostilbene at the indicated concentrations (X).

The present disclosure is directed generally to methods of using compositions of pterostilbene and methods for using the same for immune modulation against cancer. Specifically, the disclosure teaches compositions of pterostilbene and methods of using the same for the following aspects of tumor immunology/oncology: a) modulating immune activity against tumors (i.e. stimulating endogenous anti-cancer immunity); b) modulating immune efficacy of cancer therapies; and, c) modulating multi-organ and -tissue toxicity of cancer therapies, including chemotherapy, immunotherapy, radiation therapy, and targeted therapy, in cancer patients.

Trans-pterostilbene (trans-3,5-dimethoxy-4'-hydroxy-trans-stilbene, t-PTER), TMS (3,4',5-trimethoxy-trans-stilbene), 3,4',4-DH-5-MS (3,4'-dihydroxy5-methoxy-transstilbene) and 3,5-DH-4'MS (3,5-dihydroxy-4'-,ethoxy-trans-stilbene) are compounds chemically related to resveratrol.

Pterostilbene is classified as a phytoalexin, which is an antimicrobial substance that is part of a plant's defense system and is synthesized in response to pathogen infection, as well as to excessive ultraviolet exposure (Bavaresco, L., et al., Stilbene compounds: from the grapevine to wine. Drugs Exp Clin Res, 1999. 25(2-3): p. 57-63). Pterostilbene is known to have diverse benefits for the prevention and treatment of wide variety of diseases, including cancer (Rimando, A. M. and N. Suh, Biological/chemopreventive activity of stilbenes and their effect on colon cancer. Planta Med, 2008. 74(13): p. 1635-43; Pan, M. H., et al., Pterostilbene inhibited tumor invasion via suppressing multiple signal transduction pathways in human hepatocellular carcinoma cells. Carcinogenesis, 2009. 30(7): p. 1234-42; Paul, S., et al., Dietary intake of pterostilbene, a constituent of blueberries, inhibits the beta-catenin/p65 downstream signaling pathway and colon carcinogenesis in rats. Carcinogenesis, 2010. 31(7): p. 1272-8) and dyslipidemia (Rimando, A. M., et al., Pterostilbene, a new agonist for the peroxisome proliferator-activated receptor alpha-isoform, lowers plasma lipoproteins and cholesterol in hypercholesterolemic hamsters. J Agric Food Chem, 2005. 53(9): p. 3403-7.), diabetes (Amarnath Satheesh, M. and L. Pari, The antioxidant role of pterostilbene in streptozotocin-nicotinamide-induced type 2 diabetes mellitus in Wistar rats. J Pharm Pharmacol, 2006. 58(11): p. 1483-90), cardiovascular disease (Park, E. S., et al., Pterostilbene, a natural dimethylated analog of resveratrol, inhibits rat aortic vascular smooth muscle cell proliferation by blocking Akt-dependent pathway. Vascul Pharmacol, 2010. 53(1-2): p. 61-7), and cognitive function degeneration (Joseph, J. A., et al., Cellular and behavioral effects of stilbene resveratrol analogues: implications for reducing the deleterious effects of aging. J Agric Food Chem, 2008. 56(22): p. 10544-51). Attributable to its antioxidant effects, pterostilbene has been demonstrated to exert actions on tumor cells through its effects in inhibiting cancer growth by altering the cell cycle and inducing apoptosis (McCormack, D. and D. McFadden, Pterostilbene and cancer: current review. J Surg Res, 2012. 173(2): p. e53-61). The citations referred to herein are all incorporated by reference in their entireties.

Phytosterols, such as resveratrol, have been studied for their effects on immune function to gauge whether their administration might confer physiological benefits against specific diseases. In general, while these compounds exhibit broad effects against inflammation, oxidation, cancer, and aging, their functions and molecular actions on T cell activation are controversial. For example, resveratrol reportedly inhibits T cell activation and modulates collagen-induced arthritis in an animal model (Zou, T., et al., Resveratrol Inhibits CD4+ T cell activation by enhancing the expression and activity of Sirt1. PLoS One, 2013. 8(9): p. e75139). The blunted T cell activity in this publication was reportedly related to upregulation of Silent Mating Type Information Regulation 2 homolog (Sirt1), a deacetylase involved in signaling pathways that controls T cell activation. Conversely, in another study, Yang et al. found that the administration of resveratrol suppresses the $CD4^+CD25^+$ cell population among $CD4^+$ cells, down-regulates the secretion of TGF-β, and enhances IFN-γ expression in $CD8^+$ T cells both ex vivo and in vivo, leading to immune stimulation (Yang, Y., et al., Resveratrol induces the suppression of tumor-derived CD4+CD25+ regulatory T cells. Int Immunopharmacol, 2008. 8(4): p. 542-7). In another publication, resveratrol protected Treg against high fat diet-induced apoptosis by reducing oxidative stress and restoring mitochondrial functional activities in Treg, thereby supporting Treg-induced immune suppressive activities (Wang, B., et al., Resveratrol preserves mitochondrial function, stimulates mitochondrial biogenesis, and attenuates oxidative stress in regulatory T cells of mice fed a high-fat diet. J Food Sci, 2014. 79(9): p. H1823-31). Therefore, the activity of phytosterols cannot be predicted in the art when administered for the purpose of modulating T cell activity or related parameters of immune function. The citations referred to herein are all incorporated by reference in their entireties.

It is known in the art that tumors can mediate oxidative stress, and also that cancer therapeutics, for example, chemotherapy, can contribute to the free radical burden in the body, leading to tissue and organ damage and a plethora of side effects experienced by patients. One skilled in the art will appreciate that, despite the roles of phytosterols such as pterostilbene as anti-oxidants, there is evidence supporting that use of antioxidants by cancer patients should be avoided in some instances (Bjelakovic, G. and C. Gluud, Surviving antioxidant supplements. J Natl Cancer Inst, 2007. 99(10): p. 742-3). Moreover, agents with anti-oxidant activity can also act as pro-oxidants depending on the concentrations of these agents that cancer cells are exposed to and, additionally, said pro-oxidants can either exert positive or negative effects against tumors (Martin-Cordero, C., et al., Pro-oxidant natural products as anticancer agents. Curr Drug Targets, 2012. 13(8): p. 1006-28). Therefore, whether administration of a given compound or natural product will have anti-cancer effects, or whether the effects of said agent will occur through anti-oxidant or pro-oxidant activities in a specific clinical scenario cannot be predicted in the art. The citations referred to herein are all incorporated by reference in their entireties.

In one embodiment, pterostilbene or a disclosed composition thereof is administered to cancer patients undergoing treatment with cancer drugs, either before, concomitant with or following cancer drug treatment. In the context of the present disclosure, conventional cancer drugs with which said pterostilbene may be administered can be selected from categories of cancer therapies including: chemotherapy, radiotherapy, immunotherapy, personalized and targeted therapies, protein-, gene-, or other small molecule therapies, surgical resection of tumors. Specifically in the realm of immunotherapy, pterostilbene or a disclosed composition thereof can be used before, concomitant with or following cancer treatments including: cancer vaccines, monoclonal antibodies, checkpoint inhibitors or cytokines. Pterostilbene or compositions thereof can also be administered to cancer patients undergoing treatment with a plurality of the aforementioned cancer drugs or to patients undergoing successive treatment cycles with various combinations of the aforementioned cancer drugs.

In a preferred embodiment, pterostilbene is administered to a cancer patient as a component of a nutraceutical composition consisting of pterostilbene, superoxide dismutase, curcumin, alpha lipoic acid, piperine, and 2-dimethylaminoethanol in a pharmaceutically acceptable carrier.

Another major aspect of the present disclosure includes a composition comprising pterostilbene, superoxide dismutase, curcumin, alpha lipoic acid, piperine, and 2-dimethylaminoethanol. In a preferred embodiment of the disclosure, said composition is formulated into capsules containing approximately 200 mg pterostilbene and 646 mg of the combination of superoxide dismutase (200 mg), curcumin (212 mg), alpha lipoic acid (100 mg), piperine (10 mg), and 2-dimethylaminoethanol (124 mg). In some embodiments, a capsule is formulated comprising 100 mg pterostilbene and 323 mg of the combination of superoxide dismutase (100 mg), curcumin (106 mg), alpha lipoic acid (50 mg), piperine (5 mg), and 2-dimethylaminoethanol (62 mg). In some embodiments, the capsule further comprises one or more binders, including, for example, magnesium stearate and fine rice flour. In some embodiments, a capsule comprising 100 mg of pterostilbene comprises 10 mg magnesium stearate and 70 mg fine rice flour.

The formulation of pterostilbene that is administered is preferably isolated from a plant material, with said composition containing at least 0.75 wt. % pterostilbene component based on the dry weight of the plant isolate.

The pterostilbene component is preferably isolated from plant material, particularly from the heartwood, wood and/or bark of plants. Preferred plant material for obtaining the pterostilbene component are selected from the group consisting of *Guibourtia* plants, *Pterocarpus* plants, *Vitis* plants and *Dracaena* plants. More preferably the plant material is selected from the group consisting of *Guibourtia tessmanii*, *Pterocarpus santalinus*, *Pterocaxpus marsupium*, *Pterocarpus dalbergioides*, *Pterocarpus macrocarpus*, *Pterocarpus soyauxii*, *Pterocarpus tinctorius*, *Vitis vinefera*, *Dracaena cochinensis*, *Pterolobium hexapetalum* and *Dracaena loureiri*, even more preferably selected from the group consisting of *Guibourtia tessmanii*, *Pterocarpus santalinus*, *Pterocaxpus marsupiul*, *Vitis vinefera*, and most preferably selected from the group consisting of *Pterocarpus santalinus* and *Pterocarpus marsupium*. Pterostilbene may also be administered via *Vaccinium* berry extract. In some embodiments, the *Vaccinium* berry extract is obtained from blueberries.

The pterostilbene component used in the present method may be chemically manufactured (Rimando, A. M., et al., Cancer chemopreventive and antioxidant activities of pterostilbene, a naturally occurring analogue of resveratrol. J Agric Food Chem, 2002. 50(12): p. 3453-7, incorporated by reference herein in its entirety), biochemically produced (e.g. in fermentation processes), or be obtained from vegetable material, optionally followed by subsequent chemical modification. Subsequent chemical modification includes the preparation of precursors of pterostilbene component such as for instance glycosylation to produce glycosides of pterostilbene component or acylation to produce ester-group containing pterostilbene component.

In some embodiments, pterostilbene is prepared as a liposomal formulation. As used herein, a 'liposome" is a closed vesicle having a lipid bilayer structure. Liposomes as provided herein may be comprised of a plurality of lipids, including, for example, phospholipids and cholesterol. A liposome can encapsulate pterostilbene or compositions thereof in a state isolated from the external environment with a bimolecular membrane, and thus can protect encapsulated pterostilbene from being decomposed or metabolized. In addition, a liposome can be attached to a cell membrane and mucous membrane by controlling the composition of the liposome membrane, and thus it is possible to deliver the encapsulated pterostilbene into cells. The liposome can be prepared, for example, by using known methods such as a thin-membrane hydration method, an ultrasonification method, an ethanol injection method, an ether injection method, a reverse-phase evaporation method, a surfactant method, a freezing/thawing method, and a thin-membrane hydration-ultrasonic method. The particle diameter of the liposome can be controlled and modified by known methods such as an extrusion method, a French press method, and a homogenization method. The liposome particle diameter may vary, and may be, for example, from 20 to 1000 nm.

The disclosure provides compositions including nutraceutical ingredients disclosed herein, or a pharmaceutically acceptable salt or derivative thereof, together with one or more nutraceutically acceptable carriers, and, optionally, other therapeutic and/or prophylactic ingredients, known and used in the art. The carrier(s) must be "acceptable" in the sense of being compatible with the other ingredients of the formulation and not harmful to the recipient thereof. An oral composition can generally include an inert diluent or an edible carrier.

Pharmaceutical compositions may be those suitable for oral, rectal, bronchial, nasal, pulmonal, topical (including buccal and sub-lingual), transdermal, vaginal or parenteral (including cutaneous, subcutaneous, intramuscular, intraperitoneal, intravenous, intraarterial, intracerebral, intraocular injection or infusion) administration, or those in a form suitable for administration by inhalation or insufflation, including powders and liquid aerosol administration, or by sustained release systems. Suitable examples of sustained release systems include semipermeable matrices of solid hydrophobic polymers containing the compound of the disclosure, which matrices may be in form of shaped articles, e.g. films or microcapsules.

The chemical compound of the disclosure, together with a conventional adjuvant, carrier, or diluent, may thus be placed into the form of pharmaceutical compositions and unit dosages thereof. Such forms include solids, and in particular tablets, filled capsules, powder and pellet forms, and liquids, in particular aqueous or non-aqueous solutions, suspensions, emulsions, elixirs, and capsules filled with the same, all for oral use, suppositories for rectal administration, and sterile injectable solutions for parenteral use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed.

Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material.

In powders, the carrier is a finely divided solid, which is in a mixture with the finely divided active component. In tablets, the active component is mixed with the carrier having the necessary binding capacity in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration Liquid preparations include solutions, suspensions, and emulsions, for example, water or water-propylene glycol solutions. For example, parenteral injection liquid preparations can be formulated as solutions in aqueous polyethylene glycol solution. The chemical compound according to the present disclosure may thus be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulation agents such as suspending, stabilizing and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

For topical administration to the epidermis the chemical compound of the disclosure may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents.

Compositions suitable for topical administration in the mouth include lozenges comprising the active agent in a flavored base, usually sucrose and acacia or tragacanth; pastilles comprising the active ingredient in an inert base such as gelatin and glycerine or sucrose and acacia; and mouthwashes comprising the active ingredient in a suitable liquid carrier.

Solutions or suspensions are applied directly to the nasal cavity by conventional means, for example with a dropper, pipette or spray. The compositions may be provided in single or multi-dose form. In compositions intended for administration to the respiratory tract, including intranasal compositions, the compound will generally have a small particle size for example of the order of 5 microns or less. Such a particle size may be obtained by means known in the art, for example by micronization.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packaged tablets, capsules, and powders in vials or ampoules. Also, the unit dosage form can be a capsule, tablet, cachet, or lozenge itself, or it can be the appropriate number of any of these in packaged form.

Tablets, capsules and lozenges for oral administration and liquids for intravenous administration and continuous infusion are preferred compositions. Solutions or suspensions for application to the nasal cavity or to the respiratory tract are preferred compositions. Transdermal patches for topical administration to the epidermis are preferred.

Further details on techniques for formulation and administration may be found in the latest edition of Remington's Pharmaceutical Sciences (Maack Publishing Co., Easton, Pa.).

As used herein, "therapeutically effective amount" refers to an amount, e.g., of a therapeutic composition, that is sufficient to treat or ameliorate, begin to palliate, stabilize, reverse or slow progression of a disease, or otherwise reduce pathological consequences of the disease or in some manner reduce the symptoms associated with a disease or disorder. In any case, an effective amount may be given in single or divided doses. The term "therapeutically effective," when used with reference to a method, means that the method is sufficiently effective to treat or ameliorate, begin to palliate, stabilize, reverse or slow progression of a disease, in this case, cancer, or otherwise reduce pathological consequences of the disease or in some manner reduce the symptoms associated with cancer or cancer treatment in the context of the disclosure. In some embodiments, an effective amount of pterostilbene is an amount sufficient to increase an anti-tumor immune response in a subject. In some embodiments, an effective amount of pterostilbene is an amount sufficient to increase, boost, or augment cytokine secretion. In some embodiment, an effective amount of pterostilbene is an amount sufficient to block oxidative stress, thereby increasing or augmenting T-cell function. In some embodiments, an effective amount of pterostilbene is a daily dose of about 1, 2, 3, 4, 5, 6, 7, 8, 9, 10, 15, 20, 25, 30, 35, 40, 45, 50, 60, 70, 80, 90, 100, 110, 120, 130, 140, 150, 160, 170, 180, 190, 200, 250, 300, 350, 400, 450, 500, 600, 700, 800, 900, 1000, 1100, 1200, 1300, 1400, 1500, 1600, 1700, 1800, 1900, or 2000 mg, or a value within a range defined by any two of the aforementioned values. In some embodiments, an effective amount of pterostilbene increases an immune response in a subject, without killing cancer cells.

As used herein, the term "without killing" refers to an ability of an effective amount of pterostilbene to halt, neutralize, render benign, or otherwise incapacitate the malignancy of cancer cells without eradicating the cells entirely. Thus, in some embodiments, an effective amount of pterostilbene that increases an immune response without killing cancer cells may inhibit proliferation of cancer cells, induce other cells to inhibit proliferation of cancer cells, kill blood vessel cells associated with the cancer, induce other immune cells to kill blood vessel cells associated with the cancer, block proliferation of blood vessel cells associated with the cancer, or induce other immune cells to block proliferation of blood vessel cells associated with the cancer. In some embodiments, an effective amount of pterostilbene that increases an anti-tumor immune response without killing tumor cells does not cause direct cytotoxicity to the tumor cells.

As used herein, the term "treatment" refers to at least an amelioration of the symptoms associated with the aberrant immune response in the patient is achieved, where amelioration is used in a broad sense to refer to at least a reduction in the magnitude of a parameter, e.g. symptom, associated with the condition being treated. As such, "treatment" also includes situations where the disease, disorder, or pathological condition, or at least symptoms associated therewith, are completely inhibited, e.g. prevented from happening, or stopped, e.g. terminated, such that the patient no longer suffers from the condition, or at least the symptoms that characterize the condition.

The dosage of compound used in accordance with the disclosure varies depending on the compound and the type of cancer being treated. The age, lean body weight, total weight, body surface area, and clinical condition of the recipient patient; and the experience and judgment of the clinician or practitioner administering the therapy are among the factors affecting the selected dosage. Other factors include the route of administration, the patient's medical history, and the potency of the particular compound. The dosage may be varied by titration of the dosage to the particular circumstances of this disclosure to produce the desired therapeutic effect.

A used herein, the term "oxidative status" generally refers to the balance of pro-oxidant and anti-oxidant metabolites in a cell/tissue, tumor, patient, or other mammal. The term "oxidative stress" refers to the balance between the generation and elimination of reactive oxygen species, in favor of the former. In the context of the present, the ability of an ingredient or composition to alter or modulate oxidative status in a patient or to modulate oxidative stress (i.e. the concentrations of reactive oxygen species) refers to any changes said ingredient or composition imparts on free radical generation, utilization or activity. Pterostilbene or compositions thereof may modulate oxidative stress (or oxidative status) by acting as a "pro-oxidant" (i.e. by increasing the levels of reactive oxygen species). Pterostilbene or compositions thereof may alternatively modulate oxidative stress or oxidative status in a mammal by serving as anti-oxidants, referring to a reduction in free radical concentrations and their biological effects in said mammal. In this way, pterostilbene blocks oxidative stress, thus augmenting T-cell function.

In a preferred embodiment, pterostilbene is present in a nutraceutical composition in an amount sufficient to eliminate or reduce side effects and toxicity associated with chemotherapy and/or immunotherapy for treating cancer. In one embodiment, pterostilbene is administered in capsules at a dose of 200 mg to be administered to a patient at least twice daily. In a further embodiment, capsules contain pterostilbene (200 mg) in combination with superoxide dismutase, curcumin, 2-dimethylaminoethanol (DMAE), alpha lipoic acid, and piperine.

The active ingredients may be administered in one or several doses per day. A satisfactory result can, in certain instances, be obtained at a dosage as low as the human equivalent dose (HED) of 1.6216 mg/kg p.o. or a dose of about 97 mg/day p.o. for a 60 kg human patient to a dose of about 291 mg/day p.o. for a 60 kg human patient. Given that pterostilbene has a half-life of approximately 2 hr, an appropriate range can be from about 200 mg/day p.o. to about 1000 mg/day p.o. for said human patient.

In one embodiment, pterostilbene is administered to a patient with cancer who is concurrently undergoing treatment with one or more drugs for treating said cancer. Said pterostilbene is administered to the patient with cancer before, during, and/or after the cancer drug regimen.

The compositions and methods disclosed herein can be utilized in conjunction with one or more of the following chemotherapeutic agents: alkylating agents such as ifosfamide, nimustine hydrochloride, cyclophosphamide, dacarbazine, melphalan, and ranimustine, antimetabolites such as gemcitabine hydrochloride, enocitabine, cytarabine ocfosfate, a cytarabine formulation, tegafur/uracil, a tegafur/gimeracil/oteracil potassium mixture, doxifluridine, hydroxycarbamide, fluorouracil, methotrexate, and mercaptopurine, anti-tumor antibiotics such as idarubicin hydrochloride, epirubicin hydrochloride, daunorubicin hydrochloride, daunorubicin citrate, doxorubicin hydrochloride, pirarubicin hydrochloride, bleomycin hydrochloride, peplomycin sulfate, mitoxantrone hydrochloride, and mitomycin C, alkaloids such as etoposide, irinotecan hydrochloride, vinorelbine tartrate, docetaxel hydrate, paclitaxel, vincristine sulfate, vindesine sulfate, and vinblastine sulfate, hormone therapy agents such as anastrozole, tamoxifen citrate, toremifene citrate, bicalutamide, flutamide, and estramustine phosphate, platinum complexes such as carboplatin, cisplatin, and nedaplatin, angiogenesis inhibitors such as thalidomide, neovastat, and bevacizumab, L-asparaginase, drugs inhibiting the activity or production of the tumor promoting bioactive substances, such as, for example, antibodies and antibody fragments that neutralize the above bioactive substances, and substances that suppress expression of tumor promoting bioactive substances, such as an siRNA, a ribozyme, an antisense nucleic acid (including RNA, DNA, PNA, and a composite thereof), Said cancer drugs may also include one or more of the following: Ipilimumab, Tremelimumab, Nivolumab, Pembrolizumab, Pidilizumab, MPDL3280A, MEDI4736, MSB0010718C, MGA271, IMP321, BMS-986016, BMS-663513, PF-05082566, IPH2101, KW-0761, IPH2101, KW-0761, CDX-1127, MEDI-6469, CP-870,893.

Said cancer drugs may also include one or more of the following monoclonal antibodies used for treating various types of cancer: 3F8, 8H9, Abagovomab, Abituzumab, Adecatumumab, Afutuzumab, Amatuximab, Anatumomab mafenatox, Anetumab ravtansine, Apolizumab, Arcitumomab, Ascrinvacumab, Atezolizumab, Bavituximab, Bevacizumab, Bivatuzumab mertansine, Blinatumomab, Brentuximab vedotin, Brolucizumab, Brontictuzumab, Cantuzumab mertansine, Cantuzumab ravtansine, Catumaxomab, Cetuximab, Cixutumumab, Zatuximab, Votumumab, Vorsetuzumab mafodotin, Volociximab, Vanucizumab, Vantictumab, Vandortuzumab vedotin, Urelumab, Ulocuplumab, Ublituximab, Tucotuzumab celmoleukin, Tremelimumab, TRBS07, Trastuzumab, Tigatuzumab, Ticilimumab, Tenatumomab, Tarextumab, Taplitumomab paptox, Tacatuzumab tetraxetan, Sofituzumab vedotin, Siltuximab, SGN-CD33A, SGN-CD19A, Sibrotuzumab, Robatumumab, Rituximab, Rilotumumab, Ramucirumab, Radretumab, Pritumumab, Pidilizumab, Pertuzumab Omnitarg, Lumretuzumab, Isatuximab, Ipilimumab, Enavatuzumab, Edrecolomab, Duligotumab, and Clivatuzumab.

Cancer drugs can have significant toxicity and side effects in mammals. Moreover, as multiple drugs/agents are administered to a given patient for treating their cancer, the drug interactions, side effects, and risks of damage to organs/tissues increase and can be additive. Organ toxicities and adverse side effects experienced by patients include but are not limited to the following: pain, nausea, vomiting, diarrhea, anemia, lymphedema, incontinence, nephrotoxicity, thrombocytopenia, bone marrow failure, thrombotic events, capillary leak syndrome, and susceptibility to infections.

In one embodiment, pterostilbene is administered to a cancer patient over the duration of their cancer therapy in order to increase the patient's tolerability of their cancer therapy. In the context of the disclosure, a patient's tolerability to said drug therapy might be manifested as improvements in side effects experienced by said patient and reduced oxidative stress as measured by serum biomarkers), which is indicative of systemic damage caused by said drugs. In the context of the disclosure, improvements in the patient's tolerability to said drug therapy is intended to reflect increased ability of the patient to tolerate higher doses of said cancer drug therapy, ability to tolerate prolonged treatment with said cancer drugs, and/or the ability of the patient to tolerate different combinations of drugs. Here, increased tolerability can be defined by comparison to either the standard of care for treatment of the same type/stage of cancer or as compared to the same patient prior to treatment with a pterostilbene-containing composition.

In the art, many combination cancer therapies cause side effects and toxicities, and patients exhibit variable tolerance to these effects. For example, anthracycline plus trastuzumab (Herceptin) is poorly tolerated by patients diagnosed with HER2/neu expressing breast cancer where the additive effects of these agents can invoke cardiotoxicity. Risk can be lowered by sequential administration of anthracycline followed by trastuzumab, but previous anthracycline exposure also appears to increase the risk of trastuzumab-induced cardiotoxicity (Seidman, A., et al., Cardiac dysfunction in the trastuzumab clinical trials experience. J Clin Oncol, 2002. 20(5): p. 1215-21; Farolfi, A., et al., Trastuzumab-induced cardiotoxicity in early breast cancer patients: a retrospective study of possible risk and protective factors. Heart, 2013. 99(9): p. 634-9; Russo, G., et al., Role of renal function on the development of cardiotoxicity associated with trastuzumab-based adjuvant chemotherapy for early breast cancer. Intern Emerg Med, 2012. 7(5): p. 439-46; Cochet, A., et al., Baseline diastolic dysfunction as a predictive factor of trastuzumab-mediated cardiotoxicity after adjuvant anthracycline therapy in breast cancer. Breast Cancer Res Treat, 2011. 130(3): p. 845-54). In a review of clinical trials involving trastuzumab-induced cardiotoxicity, the incidence of cardiotoxicity was highest in patients receiving concomitant trastuzumab and anthracycline plus cyclophosphamide at 27%. Evaluation of the available data suggested that the rate of cardiotoxicity and symptom severity was reduced by temporal separation of anthracycline and trastuzumab administration (Seidman, A., et al., Cardiac dysfunction in the trastuzumab clinical trials experience. J Clin Oncol, 2002. 20(5): p. 1215-21); therefore, therapy with concomitant anthracycline and trastuzumab is avoided (Seidman, A., et al., Cardiac dysfunction in the trastuzumab clinical trials experience. J Clin Oncol, 2002. 20(5): p. 1215-21; Moja, L., et al., Trastuzumab containing regimens for early breast cancer. Cochrane Database Syst Rev, 2012. 4: p. CD006243). The citations referred to herein are all incorporated by reference in their entireties.

Combination therapies for cancer treatment; for example, treatments involving chemotherapy and immunotherapeutic agents, are known to evoke oxidative stress mechanism leading to organ damage. Even single agent cancer treatments can be associated with toxicity. For example, experimental studies have demonstrated that trastuzumab significantly alters the expression of myocardial genes essential for DNA repair, cardiac and mitochondrial functions, which is associated with impaired left ventricular performance in mice coupled with significant ultrastructural alterations in cardiomyocytes revealed by electron microscopy (El Zarrad, M. K., et al., Trastuzumab alters the expression of genes essential for cardiac function and induces ultrastructural changes of cardiomyocytes in mice. PLoS One, 2013. 8(11): p. e79543). Trastuzumab treatment was shown to promote oxidative stress and apoptosis in myocardium of mice, and elevates serum levels of cardiac troponin-I (cTnI) and cardiac myosin light chain-1 (cMLC1). Despite the adverse events associated with oxidative stress, it is recognized in the art that pro-oxidant activities of anti-cancer agents and the reactive oxygen species produced as a result are also involved in cytotoxicity against tumor cells (Martin-Cordero, C., et al., Pro-oxidant natural products as anticancer agents. Curr Drug Targets, 2012. 13(8): p. 1006-28). The citations referred to herein are all incorporated by reference in their entireties.

In a preferred embodiment, pterostilbene and/or pterostilbene containing compositions described herein are administered to a mammal with cancer before, during, and after treatment with conventional drug therapies and/or surgical resection of tumors for the purpose of modulating oxidative status in said mammal. In one example, pterostilbene can be administered to breast cancer patients to reduce the rate of cardiotoxicity or the severity of symptoms associated with anthracycline plus trastuzumab therapy or to modify symptoms and interaction risks resulting from other combinations of chemotherapy and/or immunotherapy agents. In one embodiment, pterostilbene will be administered over the course of trastuzumab treatment to breast cancer patients. In another embodiment, pterostilbene can be administered over the course of concomitant therapy with trastuzumab and other cancer drugs to increase said cancer patient's ability to tolerate a combination of drugs administered together.

In one embodiment, pterostilbene or a nutraceutical composition including pterostilbene is administered to a mammal with cancer to modulate oxidative status in response to administration of cancer therapy drugs to said mammal as well as to modulate oxidative stress caused by the cancer itself. The following examples are incorporated by reference to provide means of assessing oxidative stress in an individual in need thereof. Cancer patients are known to possess elevated levels of oxidative stress as compared to healthy controls. Didžiapetrienė et al. examined 42 patients with newly diagnosed stages of I-IV primary ovary cancer. Level of malondialdehyde (MDA), which correlates with oxidative stress, and catalytic activity catalase (CAT), which is an antioxidant, were determined spectrophotometrically. Significantly lower CAT (28.2±15.5 vs. 36.1±14.6 nmol/L/min, P=0.019) activity and higher MDA levels (8.7±3.0 vs. 6.7±2.7 nmol/L, P=0.002) were observed in cancer patients compared with healthy volunteers. Both variables were not confirmed as prognostic factors according to Kaplan-Meier survival estimates (Dičžiapetrienė, J., et al., Significance of blood serum catalase activity and malondialdehyde level for survival prognosis of ovarian cancer patients. Medicina (Kaunas), 2014. 50(4): p. 204-8), incorporated by reference in its entirety.

In breast cancer, a more detailed study described enhanced oxidative stress in patients and reduction of this oxidative stress associated with tumor removal. Specifically, plasma samples were collected at diagnosis, and the systemic oxidative profile was determined by evaluating the lipid peroxidation, total antioxidant capacity of plasma (TRAP), MDA, protein carbonylation, and hydroperoxides. Nitric oxide, VEGF, and TNF alpha levels were further measured. Enhanced oxidative stress was detected in patients bearing the primary tumors, characterized by high lipid peroxidation, TRAP consumption, high carbonyl content, and elevated VEGF and TNF-α levels. After tumor removal, the systemic oxidative status presented attenuation in lipid peroxidation, MDA, VEGF, and TNF-α. The 5-year recurrence analysis indicated that all patients who relapsed presented high levels of lipid peroxidation measured by chemiluminescence at diagnosis (Herrera, A. C., et al., Impact of tumor removal on the systemic oxidative profile of patients with breast cancer discloses lipid peroxidation at diagnosis as a putative marker of disease recurrence. Clin Breast Cancer, 2014. 14(6): p. 451-9). Increased oxidative stress in cancer patients has been shown in studies of breast cancer (Wang, C., et al., Lipid peroxidation and altered anti-oxidant status in breast adenocarcinoma patients. Drug Res (Stuttg), 2014. 64(12): p. 690-2; Nourazarian, A. R., P. Kangari, and A. Salmaninejad, Roles of oxidative stress in the development and progression of breast cancer. Asian Pac J Cancer Prev, 2014. 15(12): p. 4745-51; Woditschka, S., et al., DNA double-strand break repair genes and oxidative damage in brain metastasis of breast cancer. J Natl Cancer Inst, 2014. 106(7); Karki, K., et al., Expression of serum toll-like receptor 9 and oxidative damage markers in benign and malignant breast diseases. DNA Cell Biol, 2014. 33(9): p. 630-6; Karimi, N. and V. D. Roshan, Change in adiponectin and oxidative stress after modifiable lifestyle interventions in breast cancer cases. Asian Pac J Cancer Prev, 2013. 14(5): p. 2845-50; Gupta, R. K., et al., Interactions between oxidative stress, lipid profile and antioxidants in breast cancer: a case control study. Asian Pac J Cancer Prev, 2012. 13(12): p. 6295-8; Pande, D., et al., Vascular endothelial growth factor levels in relation to oxidative damage and antioxidant status in patients with breast cancer. J Breast Cancer, 2011. 14(3): p. 181-4), squamous cell carcinoma (Huo, W., et al., Antioxidant enzyme levels in pathogenesis of oral squamous cell carcinoma (OSCC). Drug Res (Stuttg), 2014. 64(11): p. 629-32; Korde, S. D., et al., Enhanced nitrosative and oxidative stress with decreased total antioxidant capacity in patients with oral precancer and oral squamous cell carcinoma. Oncology, 2011. 80(5-6): p. 382-9), gastric cancer (Ma, Y., et al., Relation between gastric cancer and protein oxidation, DNA damage, and lipid peroxidation. Oxid Med Cell Longev, 2013. 2013: p. 543760), liver cancer (Yahya, R. S., et al., Role of interleukin-8 and oxidative stress in patients with hepatocellular carcinoma. Clin Lab, 2013. 59(9-10): p. 969-76; Li, T., et al., Glutathione S-transferase P1 correlated with oxidative stress in hepatocellular carcinoma. Int J Med Sci, 2013. 10(6): p. 683-90), kidney cancer (Pirincci, N., et al., Serum prolidase activity, oxidative stress, and antioxidant enzyme levels in patients with renal cell carcinoma. Toxicol Ind Health, 2013), lung cancer (Barreiro, E., et al., Oxidative stress and inflammation in the normal airways and blood of patients with lung cancer and COPD. Free Radic Biol Med, 2013. 65: p. 859-71; Cobanoglu, U., et al., Lipid peroxidation, DNA damage and coenzyme Q10 in lung cancer patients—markers for risk assessment? Asian Pac J Cancer Prev, 2011. 12(6): p. 1399-403; Margaret, A. L., E. Syahruddin, and S. I. Wanandi, Low activity of manganese superoxide dismutase (MnSOD) in blood of lung cancer patients with smoking history: relationship to oxidative stress. Asian Pac J Cancer Prev, 2011. 12(11): p. 3049-53), multiple myeloma (Mehdi, W. A., J. A. Zainulabdeen, and A. A. Mehde, Investigation of the antioxidant status in multiple myeloma patients: effects of therapy. Asian Pac J Cancer Prev, 2013. 14(6): p. 3663-7), head and neck cancer (Marakala, V., M. Malathi, and A. R. Shivashankara, Lipid peroxidation and antioxidant vitamin status in oral cavity and oropharyngeal cancer patients. Asian Pac J Cancer Prev, 2012. 13(11): p. 5763-5; Salzman, R., et al., High perioperative level of oxidative stress as a prognostic tool for identifying patients with a high risk of recurrence of head and neck squamous cell carcinoma. Int J Clin Oncol, 2010. 15(6): p. 565-70), sarcoma (Nathan, F. M., et al., Oxidative stress and antioxidant status in primary bone and soft tissue sarcoma. BMC Cancer, 2011. 11: p. 382), prostate cancer (Guzel, S., et al., Association of Pb, Cd, and Se concentrations and oxidative damage-related markers in different grades of prostate carcinoma. Biol Trace Elem Res, 2012. 145(1): p. 23-32), and leukemia (Zelen, I., et al., Antioxidant enzymes activities and plasma levels of oxidative stress markers in B-chronic lymphocytic leukemia patients. J BUON, 2010. 15(2): p. 330-6). The compositions of pterostilbene described herein can thus be applied to modulation of oxidative stress in these clinical scenarios. The citations referred to herein are all incorporated by reference in their entireties.

One preferred embodiment is a method of augmenting anti-tumor immune responses in a cancer patient using pterostilbene and/or the compositions of pterostilbene with other ingredients described herein. Modulation of the immune response to promote anti-cancer immunity can be achieved by administration of pterostilbene or compositions thereof to cancer patients to modify the numbers or activities of one or more of the following cell types: a) B cells; b) T cells; c) innate lymphoid cells; d) natural killer cells; e) natural killer T cells; f) gamma delta T cells; g) macrophages; h) monocytes; i) dendritic cells; j) neutrophils; and k) myeloid derived suppressor cells.

The term "augment" as used herein refers to an improvement, enhancement, amplification, or strengthening of an immune response in a cancer patient, and relates to a measurable improvement in response of the patient. Thus, in some aspects, augmenting anti-tumor immune responses, for example, refers to a measurable improvement in the anti-tumor immune response of the subject. Augment can also refer to an increase in production of an immune modulatory agent, such as an increase in cytokine production, for example. Augment includes an improvement, an increase, or an enhancement as compared to a control of 0.5%, 1%, 2%, 3%, 4%, 5%, 6%, 7%, 8%, 9%, 10%, 15%, 20%, 25%, 30%, 40%, 50%, 75%, 100%, 150%, 200%, 250%, or greater, or a value with a range defined by any two of the aforementioned values.

In one major aspect, pterostilbene and/or the compositions described herein are administered to a cancer patient to suppress the numbers or functions of regulatory T cells (Treg), which have suppressive functions in the immune system.

The terms "suppression," "inhibition" and "prevention" are used herein in accordance with accepted definitions in the context of an immune response. For example, "suppression" results when an ongoing immune response is blocked or significantly reduced as compared with the level of immune response that results absent treatment, e.g., by the Treg cells disclosed herein. "Inhibition" refers to blocking the occurrence of an immune response or significantly reducing such response as compared with the level of immune response that results absent treatment, e.g., by the Treg cells disclosed herein. When administered prophylactically, such blockage may be complete so that no targeted immune response occurs, typically referred to as a "prevention" with regard to completely blocking the immune response before onset; or in the present disclosure, the treatment may advantageously reduce the effect as compared to the normal untreated state, typically referred to as suppression or inhibition.

As used herein, the terms "regulatory T cell," "T-regulatory cell" and "Treg cell" are used interchangeably, and refer to T cells that express CD4+CD25+ phenotype. In some embodiments, the Treg cells also express the FoxP3 transcription factor as measured by methods known in the art, e.g., flow cytometry, Western blot, FoxP3 mRNA transcript detected in vitro or in vivo, etc.

Regulatory T cells (Tregs) play a critical role in the maintenance of peripheral self-tolerance through their roles in suppressing the functions of activated immune cells. Naturally occurring CD4+CD25+ Tregs are produced in the thymus and express FoxP3, a transcriptional factor required for establishment and maintenance of Treg lineage identity and suppressor function. Tregs can accumulate at a disease site, where they suppress the effector function of disease specific T cells. Accordingly, increased densities of tumor-infiltrating FoxP3+ Tregs have been associated with poor prognosis in various solid tumors, including pancreatic, ovarian, and hepatocellular carcinoma. Depletion of Tregs results in enhanced antitumor immunity and tumor rejection in murine models but may also result in the development of autoimmune diseases. In the context of the present disclosure, pterostilbene or compositions containing pterostilbene described herein can be administered to cancer patients to repress the activity of Treg.

In one embodiment, a method includes providing means to allow for effective induction of tumor immunity through vaccination by induction of re-expression of TCR zeta chain, which is a key signaling molecule in activated T cells that is downregulated in cancer. Immunization may be performed against known tumor antigens to which humoral and cellular based immune responses are known, which include epidermal growth factor receptors (HER2), carcinoembryonic antigen (CEA), mucin (MUC1), the tumor suppressor protein p53, and telomerase reverse transcriptase (TERT) (Angelopoulou, K., et al., p53 gene mutation, tumor p53 protein overexpression, and serum p53 autoantibody generation in patients with breast cancer. Clin Biochem, 2000. 33(1): p. 53-62; Disis, M. L., et al., Generation of T-cell immunity to the HER-2/neu protein after active immunization with HER-2/neu peptide-based vaccines. J Clin Oncol, 2002. 20(11): p. 2624-32; Disis, M. L., et al., Generation of immunity to the HER-2/neu oncogenic protein in patients with breast and ovarian cancer using a peptide-based vaccine. Clin Cancer Res, 1999. 5(6): p. 1289-97; Goydos, J. S., et al., A phase I trial of a synthetic mucin peptide vaccine. Induction of specific immune reactivity in patients with adenocarcinoma. J Surg Res, 1996. 63(1): p. 298-304; Sandmaier, B. M., et al., Evidence of a cellular immune response against sialyl-Tn in breast and ovarian cancer patients after high-dose chemotherapy, stem cell rescue, and immunization with Theratope STn-KLH cancer vaccine. J Immunother, 1999. 22(1): p. 54-66; Tilkin, A. F., et al., Primary proliferative T cell response to wild-type p53 protein in patients with breast cancer. Eur J Immunol, 1995. 25(6): p. 1765-9; Jager, D., et al., Identification of tumor antigens as potential target antigens for immunotherapy by serological expression cloning. Cancer Immunol Immunother, 2004. 53(3): p. 144-7; Ko, B. K., et al., Clinical studies of vaccines targeting breast cancer. Clin Cancer Res, 2003. 9(9): p. 3222-34; Musselli, C., et al., Reevaluation of the cellular immune response in breast cancer patients vaccinated with MUC1. Int J Cancer, 2002. 97(5): p. 660-7; Tsuboi, A., et al., Enhanced induction of human WT1-specific cytotoxic T lymphocytes with a 9-mer WT1 peptide modified at HLA-A*2402-binding residues. Cancer Immunol Immunother, 2002. 51(11-12): p. 614-20). It is known that tumor specific antigens generally initiate an immune response by activation of the sensory component of the immune system. Specifically dendritic cells are known to infiltrate tumors and are associated with increased immunity to tumors (Hu, M., et al., Decreased intratumoral Foxp3 Tregs and increased dendritic cell density by neoadjuvant chemotherapy associated with favorable prognosis in advanced gastric cancer. Int J Clin Exp Pathol, 2014. 7(8): p. 4685-94; Ayari, C., et al., High level of mature tumor-infiltrating dendritic cells predicts progression to muscle invasion in bladder cancer. Hum Pathol, 2013. 44(8): p. 1630-7; Liska, V., et al., Infiltration of colorectal carcinoma by S100+ dendritic cells and CD57+ lymphocytes as independent prognostic factors after radical surgical treatment. Anticancer Res, 2012. 32(5): p. 2129-32; Ayari, C., et al., Bladder tumor infiltrating mature dendritic cells and macrophages as predictors of response to bacillus Calmette-Guerin immunotherapy. Eur Urol, 2009. 55(6): p. 1386-95). T cells are known to stimulate dendritic cell activity. Accordingly in one embodiment, protection of TCR-zeta chain integrity by modulation of oxidative stress is utilized to increase dendritic cell infiltration of tumors, and thus in turn stimulate antitumor immunity. The importance of preserving dendritic cell activity in the context of the disclosure is associated with the key importance of the dendritic cell (DC) in orchestration of immune response. DCs are tissue-fixed cells that are interspersed throughout the body. When DCs are activated through contacting an antigen, they migrate to the local lymph node where they activate the synthesis part of the immune system, i.e., the T cells (Gluckman, J. C., et al., In vitro generation of human dendritic cells and cell therapy. Cytokines Cell Mol Ther, 1997. 3(3): p. 187-96). The citations referred to herein are all incorporated by reference in their entireties.

One particular embodiment involves the administration pterostilbene and/or compositions thereof capable of reversing immune suppression seen in many cancer patients. Immune suppression by cancer has been well documented in advanced cancer patients possessing a variety of malignancies (Ng, C. S., et al., Mechanisms of immune evasion by renal cell carcinoma: tumor-induced T-lymphocyte apoptosis and NFkappaB suppression. Urology, 2002. 59(1): p. 9-14; Campbell, J. D., et al., Suppression of IL-2-induced T cell proliferation and phosphorylation of STAT3 and STAT5 by tumor-derived TGF beta is reversed by IL-15. J Immunol, 2001. 167(1): p. 553-61; Beck, C., H. Schreiber, and D. Rowley, Role of TGF-beta in immune-evasion of cancer. Microsc Res Tech, 2001. 52(4): p. 387-95; Almand, B., et al., Increased production of immature myeloid cells in cancer patients: a mechanism of immunosuppression in cancer. J Immunol, 2001. 166(1): p. 678-89; Dix, A. R., et al., Immune defects observed in patients with primary malignant brain tumors. J Neuroimmunol, 1999. 100(1-2): p. 216-32; Kiessling, R., et al., Tumor-induced immune dysfunction. Cancer Immunol Immunother, 1999. 48(7): p. 353-62; Kim, H. J., J. K. Park, and Y. G. Kim, Suppression of NF-kappaB activation in normal T cells by supernatant fluid from human renal cell carcinomas. J Korean Med Sci, 1999. 14(3): p. 299-303; Ungefroren, H., et al., Immunological escape mechanisms in pancreatic carcinoma. Ann N Y Acad Sci, 1999. 880: p. 243-51). Correlation between immune suppression and poor prognosis has been extensively noted (Fischer, J. R., et al., Decrease of interleukin-2 secretion is a new independent prognostic factor associated with poor survival in patients with small-cell lung cancer. Ann Oncol, 1997. 8(5): p. 457-61; Ishigami, S., et al., CD3-zetachain expression of intratumoral lymphocytes is closely related to survival in gastric carcinoma patients. Cancer, 2002. 94(5): p. 1437-42; Marana, H. R., et al., Reduced immunologic cell performance as a prognostic parameter for advanced cervical cancer. Int J Gynecol Cancer, 2000. 10(1): p. 67-73). Several means of tumor suppression of immune response are known. For example, a variety of tumor cells possess the ability to induce cleavage of the T cell receptor zeta (TCR-zeta) chain through a caspase-3 dependent manner (Gastman, B. R., et al., Tumor-induced apoptosis of T lymphocytes: elucidation of intracellular apoptotic events. Blood, 2000. 95(6): p. 2015-23; Takahashi, A., et al., Elevated caspase-3 activity in peripheral blood T cells coexists with increased degree of T-cell apoptosis and down-regulation of TCR zeta molecules in patients with gastric cancer. Clin Cancer Res, 2001. 7(1): p. 74-80). Since TCR-zeta is critical for signal transduction, host T cells become unable to respond to tumor antigens. Originally, the TCR-zeta cleavage was described in tumor bearing mice (Mizoguchi, H., et al., Alterations in signal transduction molecules in T lymphocytes from tumor-bearing mice. Science, 1992. 258(5089): p. 1795-8; Horiguchi, S., et al., Primary chemically induced tumors induce profound immunosuppression concomitant with apoptosis and alterations in signal transduction in T cells and NK cells. Cancer Res, 1999. 59(12): p. 2950-6) and subsequently in patients (Schmielau, J. and O. J. Finn, Activated granulocytes and granulocyte-derived hydrogen peroxide are the underlying mechanism of suppression oft-cell function in advanced cancer patients. Cancer Res, 2001. 61(12): p. 4756-60; Kim, C. W., et al., Alteration of signal-transducing molecules and phenotypical characteristics in peripheral blood lymphocytes from gastric carcinoma patients. Pathobiology, 1999. 67(3): p. 123-8; Laytragoon-Lewin, N., et al., Alteration of cellular mediated cytotoxicity, T cell receptor zeta (TcR zeta) and apoptosis related gene expression in nasopharyngeal carcinoma (NPC) patients: possible clinical relevance. Anticancer Res, 2000. 20(2B): p. 1093-100; Taylor, D. D., et al., Modulation of TcR/CD3-zeta chain expression by a circulating factor derived from ovarian cancer patients. Br J Cancer, 2001. 84(12): p. 1624-9; Chen, X., et al., Impaired expression of the CD3-zeta chain in peripheral blood T cells of patients with chronic myeloid leukaemia results in an increased susceptibility to apoptosis. Br J Haematol, 2000. 111(3): p. 817-25; Healy, C. G., et al., Impaired expression and function of signal-transducing zeta chains in peripheral T cells and natural killer cells in patients with prostate cancer. Cytometry, 1998. 32(2): p. 109-19). The correlation between suppressed TCR-zeta and suppressed IFN-gamma production has been reported, implying functional consequences (Kim, C. W., et al., Alteration of signal-transducing molecules and phenotypical characteristics in peripheral blood lymphocytes from gastric carcinoma patients. Pathobiology, 1999. 67(3): p. 123-8). The cause of TCR-zeta suppression has been attributed, at least in part, to reactive oxygen radicals produced as a result of several factors:

A) The inflammatory activity occurring inside the tumor (it is well established that there is a constant area of necrosis intratumorally);
B) Macrophages associated with the tumor; and
C) Neutrophils activated directly by the tumor, or by the tumor associated macrophages.

The citations referred to herein are incorporated by reference in their entireties.

Tumors are usually associated with macrophage infiltration, which is correlated with tumor stage and is believed to contribute to tumor progression by stimulation of angiogenesis (Valkovic, T., et al., Correlation between vascular endothelial growth factor, angiogenesis, and tumor-associated macrophages in invasive ductal breast carcinoma. Virchows Arch, 2002. 440(6): p. 583-8; Makitie, T., et al., Tumor-infiltrating macrophages (CD68(+) cells) and prognosis in malignant uveal melanoma. Invest Ophthalmol Vis Sci, 2001. 42(7): p. 1414-21; Leek, R. D., et al., Association of macrophage infiltration with angiogenesis and prognosis in invasive breast carcinoma. Cancer Res, 1996. 56(20): p. 4625-9). Cytokines such as M-CSF (Valkovic, T., et al., Correlation between vascular endothelial growth factor, angiogenesis, and tumor-associated macrophages in invasive ductal breast carcinoma. Virchows Arch, 2002. 440(6): p. 583-8) and VEGF (Lewis, J. S., et al., Expression of vascular endothelial growth factor by macrophages is up-regulated in poorly vascularized areas of breast carcinomas. J Pathol, 2000. 192(2): p. 150-8) produced by tumor infiltrating macrophages are essential for tumor progression to malignancy. In fact, tumors implanted into M-CSF deficient op/op mice (that lack macrophages) do not metastasize or become vascularized (Nowicki, A., et al., Impaired tumor growth in colony-stimulating factor 1 (CSF-1)-deficient, macrophage-deficient op/op mouse: evidence for a role of CSF-1-dependent macrophages in formation of tumor stroma. Int J Cancer, 1996. 65(1): p. 112-9). Tumor-associated macrophages possess an activated phenotype and release various inflammatory mediators such as cyclo-oxygenase metabolites (Kamate, C., et al., Inflammation and cancer, the mastocytoma P815 tumor model revisited: triggering of macrophage activation in vivo with pro-tumorigenic consequences. Int J Cancer, 2002. 100(5): p. 571-9; Young, M. R., et al., Suppressor alveolar macrophages in mice bearing metastatic Lewis lung carcinoma tumors. J Leukoc Biol, 1987. 42(6): p. 682-8), TNF-alpha (Billingsley, K G., et al., Macrophage-derived tumor necrosis factor and tumor-derived of leukemia inhibitory factor and interleukin-6: possible cellular mechanisms of cancer cachexia. Ann Surg Oncol, 1996. 3(1): p. 29-35), and IL-6 (Bonta, I. L. and S. Ben-Efraim, Involvement of inflammatory mediators in macrophage antitumor activity. J Leukoc Biol, 1993. 54(6): p. 613-26) which lead to increased levels of oxidative stress produced by host immune cells. In addition, tumor associated macrophages themselves produce large amounts of free radicals such as NO, OH, and $H_2O_2$ (Bhaumik, S. and A. Khar, Induction of nitric oxide production by the peritoneal macrophages after intraperitoneal or subcutaneous transplantation of AK-5 tumor. Nitric Oxide, 1998. 2(6): p. 467-74; Lewis, J. G. and D. O. Adams, Inflammation, oxidative DNA damage, and carcinogenesis. Environ Health Perspect, 1987. 76: p. 19-27; Kono, K, et al., Hydrogen peroxide secreted by tumor-derived macrophages down-modulates signal-transducing zeta molecules and inhibits tumor-specific T cell- and natural killer cell-mediated cytotoxicity. Eur J Immunol, 1996. 26(6): p. 1308-13). The high levels of macrophage activation in cancer patients is illustrated by high serum levels of neopterin, a tryptophan metabolite that is associated with poor prognosis (Murr, C., et al., Neopterin as a marker for immune system activation. Curr Drug Metab, 2002. 3(2): p. 175-87). The citations above are each incorporated by reference in its entirety.

In addition to oxidative stress elaborated by tumor-associated macrophages, the presence of the tumor itself causes systemic changes associated with chronic inflammation. Erythrocyte sedimentation ration, C-reactive protein and IL-6 are markers of inflammatory stress used to designate progression of pathological immune diseases such as arthritis (Whisler, R. L., L. S. Gray, and K. V. Hackshaw, Rheumatology, a clinical overview. Clin Podiatr Med Surg, 2002. 19(1): p. 149-61, vii; Ishihara, K. and T. Hirano, IL-6 in autoimmune disease and chronic inflammatory proliferative disease. Cytokine Growth Factor Rev, 2002. 13(4-5): p. 357). Interestingly advanced cancer patients possess all of these inflammatory markers (Mahmoud, F. A. and N. I. Rivera, The role of C-reactive protein as a prognostic indicator in advanced cancer. Curr Oncol Rep, 2002. 4(3): p. 250-5; Smith, P. C., et al., Interleukin-6 and prostate cancer progression. Cytokine Growth Factor Rev, 2001. 12(1): p. 33-40; Rutkowski, P., et al., Cytokine serum levels in soft tissue sarcoma patients: correlations with clinico-pathological features and prognosis. Int J Cancer, 2002. 100(4): p. 463-71; Kallio, J. P., et al., Soluble immunological parameters and early prognosis of renal cell cancer patients. J Exp Clin Cancer Res, 2001. 20(4): p. 523-8 Ljungberg, B., K. Grankvist, and T. Rasmuson, Serum interleukin-6 in relation to acute-phase reactants and survival in patients with renal cell carcinoma. Eur J Cancer, 1997. 33(11): p. 1794-8). Another marker of chronic inflammation is decreased albumin synthesis by the liver; this is also seen in cancer patients and is believed to contribute, at least in part, to cachexia (Fearon, K. C., et al., Pancreatic cancer as a model: inflammatory mediators, acute-phase response, and cancer cachexia. World J Surg, 1999. 23(6): p. 584-8; McMillan, D. C., et al., Albumin concentrations are primarily determined by the body cell mass and the systemic inflammatory response in cancer patients with weight loss. Nutr Cancer, 2001. 39(2): p. 210-3). In addition, the inflammatory marker fibrinogen D-dimers is also higher in cancer patients as opposed to controls (Oya, M., et al., High preoperative plasma D-dimer level is associated with advanced tumor stage and short survival after curative resection in patients with colorectal cancer. Jpn J Clin Oncol, 2001. 31(8): p. 388-94; Ferrigno, D., G. Buccheri, and I. Ricca, Prognostic significance of blood coagulation tests in lung cancer. Eur Respir J, 2001. 17(4): p. 667-73; Blackwell, K., et al., Plasma D-dimer levels in operable breast cancer patients correlate with clinical stage and axillary lymph node status. J Clin Oncol, 2000. 18(3): p. 600-8). Schmielau et al. reported that in patients with a variety of cancers, activated neutrophils are circulating in large numbers (Schmielau, J. and O. J. Finn, Activated granulocytes and granulocyte-derived hydrogen peroxide are the underlying mechanism of suppression of t-cell function in advanced cancer patients. Cancer Res, 2001. 61(12): p. 4756-60). These neutrophils secrete reactive oxygen radicals such as hydrogen peroxide, which trigger cleavage of TCR-zeta and suppressed IFN-gamma production. This was demonstrated by co-incubation of the neutrophils from cancer patients with lymphocytes from healthy volunteer. A profound suppression of TCR-zeta expression was seen. Evidence for the critical role of hydrogen peroxide was shown by the fact that addition of catalase suppressed TCR-zeta chain downregulation. Accordingly, the disclosure teaches means of decreasing oxidative stress by administration of pterostilbene or pterostilbene containing compounds as a means of restoring TCR-zeta chain expression and interferon gamma production by T cells, thereby improving anti-tumor responses. The citations above are each incorporated by reference in its entirety.

In one embodiment, pterostilbene or pterostilbene containing compositions are utilized to decrease neutrophil activation in cancer patients, as a means of restoring anti-tumor immunity. Methods of assessing the number of circulating activated neutrophils are known in the art and can be applied to measure immune restoration in response to pterostilbene or pterostilbene containing compositions. This method involves collecting peripheral blood from patients, spinning the blood on a density gradient such as Ficoll, and collecting the lymphocyte fraction. While in healthy volunteers the lymphocyte fraction contained primarily lymphocytes, in cancer patients the lymphocyte fraction contained both lymphocytes and a large number of neutrophils. The reason why these neutrophils are present in the lymphocyte fraction is because activation alters their density so that they co-purify differently on the gradient. A potential indication of the importance of activated neutrophils to cancer progression is provided by Tabuchi et al. who show that removal of granulocytes from the peripheral blood of cancer patients resulted in reduced tumor size. Unfortunately, the study was performed in only 2 patients (Tabuchi, T., et al., Granulocyte apheresis as a possible new approach in cancer therapy: A pilot study involving two cases. Cancer Detect Prev, 1999. 23(5): p. 417-21), incorporated by reference herein in its entirety.

The present disclosure can be applied to improve both the efficacy and safety of immune checkpoint inhibitors by administering pterostilbene or compositions including pterostilbene described herein during the course of cancer therapy with immune checkpoint inhibitors. Under physiological conditions, immune checkpoints function to prevent aberrantly activated T-cells from mediating autoimmunity; however, they also negatively regulate anti-tumor T cell responses, leading to T cell "exhaustion." (Datta, J., et al., Rationale for a Multimodality Strategy to Enhance the Efficacy of Dendritic Cell-Based Cancer Immunotherapy. Front Immunol, 2015. 6: p. 271). The CTLA-4/B7 and PD-1/PD-L1 pathways are areas of intense investigation. CTLA-4, a CD28 homolog, is upregulated upon T-cell activation and competes with CD28 for binding to APC ligands CD80 (B7.1) and CD86 (B7.2). PD-1, a CD28/CTLA-4 homolog, is expressed on T-cells subjected to chronic antigen exposure (for example, in cancer and chronic infections). PD-1 binding to its ligands PD-L1/PD-L2—expressed on myeloid cells, DCs, stromal cells, and tumor cells—provides inhibitory signals to T cells. Moreover, PD-1:PD-L1 engagement inhibits the TCR-induced "stop signal," resulting in reduced T-cell:DC or T-cell:tumor contact; PD-1 blockade may reverse these effects, abrogate tolerance, and improve tumor targeting (Fife, B. T., et al., Interactions between PD-1 and PD-L1 promote tolerance by blocking the TCR-induced stop signal. Nat Immunol, 2009. 10(11): p. 1185-92; Diepolder, H. and R. Obst, Making antigen invisible: a coinhibitory molecule regulates the interaction between T cells and dendritic cells. Expert Rev Vaccines, 2010. 9(3): p. 243-7). Inhibitors of these immune checkpoint pathways (for example, monoclonal antibodies directed against CTLA-4) have shown clinical promise thus far. As is the problem with the majority of cancer therapeutic approaches, the challenges include tumor non-specific effects, which can manifest as dose-limiting toxicity in some patients. The side effects of checkpoint inhibitors include inflammatory effects such as uveitis, dermatitis, colitis, hepatitis, pancreatitis, and hypophysitis, requiring treatment with steroids to control these immune-related sequelae. Pterostilbene and/or compositions including pterostilbene described herein can be applied to improve patient tolerance of treatment by reducing or alleviating the abovementioned side effects. Pterostilbene and/or compositions described herein can be applied to modulate expression of CTLA-4/B7 and PD-1/PD-L1 in a manner that is conducive with re-activation of immune responses in the presence of a tumor. The citations referred to above are each incorporated by reference in its entirety.

Myeloid-derived suppressor cells (MDSCs) are a heterogeneous population of early myeloid progenitors, immature granulocytes, macrophages, and dendritic cells at different stages of differentiation. These cells are of great interest because they have the capacity to suppress both the cytotoxic activities of natural killer (NK) and NKT cells, and the adaptive immune response mediated by CD8+ T cells. While the mechanism of NK cell inhibition is currently not well understood, multiple pathways are responsible for MDSC-mediated T cell suppression including: 1) production of arginase 1/ARG1 and 2) upregulation of nitric oxide synthase 2 (NOS2). ARG1 and NOS2 metabolize L-arginine and either together, or separately, block translation of the T cell CD3 zeta chain, inhibit T cell proliferation, and promote T cell apoptosis. Additionally, MDSCs secrete immunosuppressive cytokines and induce regulatory T cell development. In mice, MDSCs are broadly defined as CD11b+Gr-1/Ly-6G+ cells, but the relative expression levels of Ly-6G and Ly-6C identify two specific subsets. Human MDSCs commonly express Siglec-3/CD33 and lack lineage markers and HLA-DR, but heterogeneous expression of CD14 and CD15 suggest that multiple subsets exist.

Also among the numerous immunological mechanisms that are re-activated in cancer are natural killer (NK) cells, which constitute a crucial arm of the innate immune system that play pivotal roles in immune surveillance against tumors. Indeed, decreased NK cell activity is associated with cancer (Yamazaki, H., et al., Changes in natural killer cell activity by external radiotherapy and/or brachytherapy. Oncol Rep, 2002. 9(2): p. 359-63; Rosenberg, S. A., Immunotherapy and gene therapy of cancer. Cancer Res, 1991. 51(18 Suppl): p. 5074s-5079s), each incorporated by reference in its entirety.

In a preferred embodiment, pterostilbene and/or pterostilbene compositions described herein is administered to enhance ADCC in a mammal undergoing monoclonal antibody therapy for cancer. One of the treatment approaches for cancer involves monoclonal antibody therapy to kill tumor cells and harness cell mediated immune mechanisms. In general, therapeutic antibodies kill tumor cells via three mechanisms where the present composition can be utilized (Scott, A. M., J. D. Wolchok, and L. J. Old, Antibody therapy of cancer. Nat Rev Cancer, 2012. 12(4): p. 278-87), incorporated by reference herein in its entirety: (1) Direct antibody action; specifically, blockade or agonist activity of ligand/receptor signaling, induction of apoptosis, and delivery of drugs or cytotoxic agents. Antibody receptor activation activity can produce direct tumor cell killing effect. For example, some antibodies can bind to receptors on the surface of tumor cells, activate the receptor, leading to apoptosis. Antibodies can also mediate tumor cell killing by receptor-antagonistic activity. For example, certain antibodies can bind to cell surface receptors and block dimerization, kinase activation and downstream signaling, thereby inhibiting proliferation and promote apoptosis. Binding of antibodies to an enzyme can lead to neutralization, signal abrogation, and cell death. (2) Immune-mediated cell killing mechanisms include complement-dependent cytotoxicity (CDC) and antibody-dependent cell-mediated cytotoxicity (ADCC) mediated by NK cells. Immune-mediated killing of tumor cells can be accomplished through numerous mechanisms, including: induction of phagocytosis, complement activation, antibody-dependent cell-mediated cytotoxicity, genetically modified T cells being targeted to the tumor by single-chain variable fragment, through antibody-mediated antigenic cross presentation to dendritic cell to activate T cells, inhibition of T cell inhibitory receptors like CTLA-4. (3) Specific effects of antibodies on the tumor endothelium and matrix, including: stromal cell inhibition, delivery of toxins to stromal cells, and delivery of toxins to the vasculature.

In a preferred embodiment, pterostilbene and/or pterostilbene compositions described herein is administered as an adjunct to treatment of cancer patients with interleukin-2 therapy. It is known in the art that IL-2 toxicity can manifest in multiple organ systems, most significantly the heart, lungs, kidneys, and central nervous system. The most common manifestation of IL-2 toxicity is capillary leak syndrome, resulting in a hypovolemic state and fluid accumulation in the extravascular space, leading to development of oliguria, ischemia, and confusion (Schwartz, R. N., L. Stover, and J. Dutcher, Managing toxicities of high-dose interleukin-2. Oncology (Williston Park), 2002. 16(11 Suppl 13): p. 11-20), incorporated by reference herein in its entirety. Capillary leak syndrome can affect more than one organ system simultaneously, contributing to the toxicity often observed in patients receiving high-dose IL-2. The release of cytokines after IL-2 administration has also been implicated as the cause of flu-like symptoms experienced by patients such as fever, chills, myalgias, and arthralgias. Pterostilbene and/or compositions described herein can be utilized to manage IL-2-associated toxicity and/or to support anti-tumor immunity in response to IL-2 treatment.

In some embodiments is provided a method of augmenting anti-tumor immune responses in a cancer patient, said method comprising the steps of: a) selecting a cancer patient; b) assessing immune response of said cancer patient; c) administering a composition containing an effective amount of pterostilbene to modulate said immune response; and d) adjusting dosage of said pterostilbene based on modulation of said immune response. In some embodiments, the immune response is assessed by assessing the function of immune cells. In some embodiments, immune cells are selected from a group consisting of B cells, T cells, innate lymphoid cells, natural killer cells, natural killer T cells, gamma delta T cells, macrophages, monocytes, dendritic cells, neutrophils, and myeloid derived suppressor cells.

As described herein B cells can be CD5+ B cells or CD5− B cells, and B cells can be naïve B cells or memory B cells.

T cells as described herein can be either CD4+ or CD8+ T cells, and can be CD28 positive T cells or CD28 negative T cells. T cells can also be either memory T cells or naïve T cells. Furthermore, T cells can be expressive of CD3. T cells can be regulatory cells. In some embodiments, T regulatory cells are expressive of proteins, including, for example CD25, CTLA-4, or FoxP3, or combinations thereof. In some embodiments, T cells are Th1 cells or Th2 cells.

As described herein, Th1 cells are capable of secreting cytokines including, for example, interferon gamma, interleukin 2, and TNF-beta. In some embodiments, Th1 cells are expressive of markers, including, for example, CD4, CD94, CD119 (IFNγ R1), CD183 (CXCR3), CD186 (CXCR6), CD191 (CCR1), CD195 (CCR5), CD212 (IL-12Rβ1&2), CD254 (RANKL), CD278 (ICOS), IL-18R, MRP1, NOTCH3, or TIM3, or combinations thereof.

As described herein, Th2 cells are capable of secreting cytokines including, for example, IL-4, IL-5, IL-6, IL-9, IL-10, or IL-13, or combinations thereof. In some embodiments, Th2 cells express markers including, for example, CRTH2, CCR4, or CCR3, or combinations thereof.

As described herein, innate lymphoid cells can be innate lymphoid cells 1, innate lymphoid cells 2, innate lymphoid cells 3, or lymphoid tissue inducer cells, or combinations thereof. Innate lymphoid cell 1 are expressive of T bet and respond to IL-12 by secretion of interferon gamma but lack expression of CD56. Innate lymphoid cell 2 produce IL-4 and IL-13. Innate lymphoid cell 3 produce IL-17a and IL-22. Lymphoid tissue inducer cells are cells involved in the induction of memory T cells.

As described herein, macrophages include M1 or M2 macrophages. In some embodiments, M1 macrophages are capable of producing nitric oxide. In some embodiments, M2 macrophages are capable of producing arginase.

As described herein, dendritic cells can be myeloid dendritic cells or lymphoid dendritic cells. In some embodiments, myeloid dendritic cells are capable of stimulating Th1 immune responses in a mature state. In some embodiments, myeloid dendritic cells in said mature state express substantially higher levels of CD80 as compared to myeloid dendritic cells in an immature state. In some embodiments, myeloid dendritic cells in said mature state express substantially higher levels of CD86 as compared to myeloid dendritic cells in an immature state. In some embodiments, myeloid dendritic cells in said mature state express substantially higher levels of CD40 as compared to myeloid dendritic cells in an immature state. In some embodiments, lymphoid dendritic cells are capable of producing interferon alpha.

In some embodiments, assessment of an immune response of immune cells is performed by quantifying anticancer activities of said immune cells. In some embodiments, anticancer activities of the immune cells are assessed by determined the immune cells' ability to directly kill cancer cells, to induce other cells to kill cancer cells, to directly inhibit proliferation of cancer cells, to induce other cells to inhibit proliferation of cancer cells, to directly kill blood vessel cells associated with the cancer, to induce other immune cells to kill blood vessel cells associated with the cancer, to directly block proliferation of blood vessel cells associated with the cancer, or to induce other immune cells to block proliferation of blood vessel cells associated with the cancer.

In some embodiments, the immune responses are associated with enhanced production of Th1 cells, or with enhanced production of Th17 cells. In some embodiments, the anticancer immune responses are associated with enhanced production and/or lytic function of NK cells.

In some embodiments, the composition is administered to a subject as a component of a nutraceutical formulation. In some embodiments, the composition containing an effective amount of pterostilbene comprises a pharmaceutically acceptable salt of pterostilbene. In some embodiments, the pterostilbene is isolated from a plant material. In some embodiments, the composition contains at least about a 0.75 wt. % pterostilbene component based on the dry weight of the plant isolate. In some embodiments, the pterostilbene is administered daily at a concentration ranging from about 0.007 to about 1500 mg pterostilbene component per kg metabolic weight. In some embodiments, pterostilbene is administered daily at a concentration of about 2.5 mg to about 10 mg of pterostilbene per kilogram of subject body weight. In some embodiments, pterostilbene is administered in capsules at a dose of about 200 mg at least twice daily. In some embodiments, pterostilbene is administered via an extract of Vaccinium berries, such as blueberries. In some embodiments, pterostilbene is administered with a combination of ingredients including, superoxide dismutase, curcumin, DMAE, alpha lipoic acid, and piperine.

In some embodiments is provided a method of preventing or reducing CD3-zeta chain downregulation in a cancer patient. In some embodiments, the method comprises assessing CD3-zeta chain expression levels in T cells in said cancer patient, administrating an effective daily amount of pterostilbene for modulating oxidative stress in said cancer patient, measuring CD3-zeta chain expression levels in T cells in said cancer patient after administration of said effective amount of pterostilbene and, adjusting said daily dosage or duration of administration of pterostilbene to maintain the prevention or reduction of CD3-zeta expression levels in T cells in said cancer patient.

In some embodiments, an effective amount of pterostilbene for modulating oxidative stress in a cancer patient is determined by quantification of serum malondialdehyde (MDA), by quantification of plasma total antioxidant capacity (TAC), by quantification of erythrocyte antioxidant enzymes, or by quantification of one or more inflammatory marker. In some embodiments, the erythrocyte antioxidant enzymes include, for example, superoxide dismutase (SOD), glutathione peroxidase (GPx), or catalase (CAT), or combinations thereof. In some embodiments, the one or more inflammatory marker includes, for example, C reactive protein (CRP), IL-1, IL-6, IL-8, IL-11, IL-17, IL-21, IL-33, TNF-alpha, lipoprotein-associated phospholipase A2 (LP-PLA2), lipoprotein Lp(a), myeloperoxidase (MPO), macrophage chemotactic protein 1 (MCP-1), oxidized low-density lipoprotein (oxidized LDL), adiponectin, matrix metalloproteases (MMP), such as MMP-9,1,2, CD40, homocysteine, cardiovascular risk factor (CVRF), plasminogen activator inhibitor (PAI-1), prostaglandin (PG), tissue polypeptide antigen (TPA), von Willebrand factor (vWF), platelet aggregation, fibrinogen, Factor VII, Factor VIII, tissue factor, phosphoglucose (PGI1), endothelin, metalloproteinases, Lipoxygenase, or angiotensin, or combinations thereof.

In some embodiments, the composition containing an effective amount of pterostilbene comprises a pharmaceutically acceptable salt of pterostilbene. In some embodiments, the pterostilbene is isolated from a plant material. In some embodiments, the composition contains at least about a 0.75 wt. % pterostilbene component based on the dry weight of the plant isolate. In some embodiments, the pterostilbene is administered daily at a concentration ranging from about 0.007 to about 1500 mg pterostilbene component per kg metabolic weight. In some embodiments, pterostilbene is administered daily at a concentration of about 2.5 mg to about 10 mg of pterostilbene per kilogram of subject body weight. In some embodiments, pterostilbene is administered in capsules at a dose of about 200 mg at least twice daily. In some embodiments, pterostilbene is administered via an extract of Vaccinium berries, such as blueberries. In some embodiments, pterostilbene is administered with a combination of ingredients including, superoxide dismutase, curcumin, DMAE, alpha lipoic acid, and piperine. In some embodiments, the pterostilbene is administered in the form of a sustained release (SR) formulation. In some embodiments, the SR formulation comprises a prodrug, or analog of N-pterostilbene, or a salt or solvate thereof. In some embodiments, the composition, upon oral administration, provides a therapeutically effective plasma concentration of pterostilbene over more than about 3 hours following the administration. In some embodiments, the pterostilbene formulation further comprises an immediate release (IR) component. In some embodiments, the IR component includes a prodrug, or analog of pterostilbene, or a salt or solvate thereof. In some embodiments, the composition, upon oral administration, provides a therapeutically effective plasma concentration of pterostilbene over about 45 minutes to about 20 hours following the administration. In some embodiments, the SR and/or IR component comprises a prodrug or analog of pterostilbene which is less polar than pterostilbene and possesses an increased absorbability profile in the lower gastrointestinal tract of a mammal. In some embodiments, the SR and/or IR component comprises a prodrug of pterostilbene selected from the group consisting of an ester prodrug, an amide prodrug, and an anhydride prodrug.

In some embodiments, the TCR-zeta chain expression is measured by Western immunoblotting. In some embodiments, preventing or reducing CD3-zeta chain downregulation in said cancer patient is performed to augment cytokine production by T cells in said cancer patient, or to augment proliferation by T cells in said cancer patient.

In some embodiments described herein is provided a method for treating or alleviating cancer associated immune dysfunction in a mammal comprising administering to an mammal in need thereof a therapeutically effective amount of a pharmaceutical or nutraceutical composition consisting essentially of isolated or chemically-synthesized pterostilbene, its pharmaceutically or nutraceutically acceptable salts or isomers thereof and a pharmaceutically or nutraceutically acceptable carrier. In some embodiments, the composition is effective to treat said cancer associated immune dysfunction in the individual.

In some embodiments is provided a method of restoring natural killer cell activity in a mammal with cancer comprising administering to a mammal in need thereof a therapeutically effective amount of a pharmaceutical or nutraceutical composition consisting essentially of isolated or chemically-synthesized pterostilbene, its pharmaceutically or nutraceutically acceptable salts or isomers thereof and a pharmaceutically or nutraceutically acceptable carrier. In some embodiments, the composition is effective to decrease the cancer associated natural killer cell defect in said mammal.

In some embodiments is provided a method of restoring monocyte activity in a mammal with cancer comprising administering to a mammal in need thereof a therapeutically effective amount of a pharmaceutical or nutraceutical composition consisting essentially of isolated or chemically-synthesized pterostilbene, its pharmaceutically or nutraceutically acceptable salts or isomers thereof and a pharmaceutically or nutraceutically acceptable carrier. In some embodiments, the composition is effective to decrease the cancer associated monocyte dysfunction in the individual.

In some embodiments is provided a method of restoring or improving T cell function in a mammal with cancer comprising administering to a mammal in need thereof a therapeutically effective amount of a nutraceutical composition consisting essentially of isolated or chemically-synthesized pterostilbene, its pharmaceutically or nutraceutically acceptable salts or isomers thereof and a pharmaceutically or nutraceutically acceptable carrier. In some embodiments, the composition is effective to decrease the cancer associated T cell dysfunction in said mammal.

In some embodiments is provided a method of decreasing type 2 macrophage mediated immune suppression in the tumor microenvironment in a mammal with cancer including administering to a mammal in need thereof a therapeutically effective amount of a pharmaceutical or nutraceutical composition consisting essentially of isolated or chemically-synthesized pterostilbene, its pharmaceutically or nutraceutically acceptable salts or isomers thereof and a pharmaceutically or nutraceutically acceptable carrier. In some embodiments, pterostilbene is administered at a sufficient amount to reduce production of PGE-2 or immune suppressive mediators by type 2 macrophages in a tumor microenvironment. In some embodiments, the immune suppressive mediators produced by type 2 macrophages include, for example, IL-1 receptor antagonist, IL-10, IL-20, polyamines, and soluble ligands of NKG2D. In some embodiments, pterostilbene is administered at a sufficient concentration to induce inhibition of angiogenesis supporting activity of type 2 macrophages. In some embodiments, angiogenesis supporting activity of type 2 macrophages is assessed by quantification of production of angiogenic cytokines. Angiogenic cytokines can include, for example VEGF, FGF, TGF-b, EGF, IGF, IL-20, or CTNF.

In some embodiments is provided a method of improving an anti-tumor immune response in a mammal with cancer. In some embodiments, the method includes modulating oxidative status in said patient by administration of a composition containing pterostilbene, stimulating a tumor-specific immune response through immunizing said mammal with a tumor-specific or tumor-associated antigen, and continuing administration of said pterostilbene containing composition so as to modulate oxidative status to allow optimal induction of antitumor immunity. In some embodiments, the tumor-specific or tumor-associated antigen is administered together with an adjuvant to increase immunogenicity. In some embodiments, the tumor-specific or tumor associated antigen includes, for example, Fos-related antigen 1, LCK, FAP, VEGFR2, NA17, PDGFR-beta, PAP, MAD-CT-2, Tie-2, PSA, protamine 2, legumain, endosialin, prostate stem cell antigen, carbonic anhydrase IX, STn, Page4, proteinase 3, GM3 ganglioside, tyrosinase, MART1, gp100, SART3, RGS5, SSX2, Globo1, Tn, CEA, hCG, PRAME, XAGE-1, AKAP-4, TRP-2, B7H3, sperm fibrous sheath protein, CYP1B1, HMWMAA, sLe(a), MAGE A1, GD2, PSMA, mesothelin, fucosyl GM1, GD3, sperm protein 17, NY-ESO-1, PAX5, AFP, polysialic acid, EpCAM, MAGE-A3, mutant p53, ras, mutant ras, NY-BR1, PAX3, HER2/neu, OY-TES1, HPV E6 E7, PLAC1, hTERT, BORIS, ML-IAP, idiotype of b cell lymphoma or multiple myeloma, EphA2, EGFRvIII, cyclin B1, RhoC, androgen receptor, surviving, MYCN, wildtype p53, LMP2, ETV6-AML, MUC1, BCR-ABL, ALK, WT1, ERG (TMPRSS2 ETS fusion gene), sarcoma translocation breakpoint, STEAP, OFA/iLRP, or Chondroitin sulfate proteoglycan 4 (CSPG4), or combinations thereof.

In some embodiments, a checkpoint inhibitor is further administered to said mammal with cancer. As described herein, a checkpoint inhibitor is an agent or a plurality of agents that suppress a molecule or cascade associated with inhibition of immune response. In some embodiments, the checkpoint inhibitor includes an inhibitor of CTLA4 activity. In some embodiments, the inhibitor of CTLA4 activity blocks or substantially interferes with binding of CTLA4 to its cognate ligand. In some embodiments, the cognate ligand of CTLA4 is CD80 or CD86. In some embodiments, the inhibitor of CTLA4 activity includes a protein, a peptide, or an aptamer. In some embodiments, the protein inhibitor of CTLA4 is an antibody. In some embodiments, the checkpoint inhibitor includes an inhibitor of PD1 activity. In some embodiments, the inhibitor of PD1 activity blocks or substantially interferes with binding of PD1 to its cognate ligand. In some embodiments, the cognate ligand of PD1 is PD1-ligand. In some embodiments, the checkpoint inhibitor is an inhibitor of PD1. In some embodiments, the inhibitor of PD1 includes a protein, a peptide, or an aptamer. In some embodiments, the protein inhibitor of PD1 is an antibody.

In some embodiments is provided a method of treating a tumor bearing mammal including administration of a therapeutically effective dose of a tumor targeting antibody together with a dose or plurality of doses of pterostilbene or a derivative thereof capable of augmenting antitumor efficacy of said tumor targeting antibody. In some embodiments, the antibody includes, for example, rituximab, trastuzumab, nimotuzumab, alemtuzumab, or gemtuzumab, or combinations thereof. In some embodiments, the antitumor efficacy of the tumor targeting antibody is augmented by improved antibody mediated cellular cytotoxicity or by improved immune responses. In some embodiments, the improved immune responses include immunological functions of T cell cytotoxicity, T cell production of tumor inhibitory/immune stimulatory cytokines, NK cell cytotoxicity, or NK production of tumor inhibitory/immune stimulatory cytokines.

In some embodiments is provided a method of treating a mammal with cancer undergoing surgery for tumor resection including: identifying a mammal with cancer in need of tumor resection; administering a therapeutically effective dose or plurality of doses of pterostilbene to said mammal, and, performing said tumor resection surgery. In some embodiments, the effective dose or plurality of doses of pterostilbene is determined on the basis of measurement of oxidative status in said mammal before and after pterostilbene administration and prior to said tumor resection surgery. In some embodiments, the oxidative status is measured in the plasma of said mammal on the basis of one or more of the following: malondialdehyde; superoxide dismutase; glutathione peroxidase, and/or, catalase. In some embodiments, the oxidative status is measured based the levels of DNA oxidation products in plasma of said mammal. In some embodiments, the DNA oxidation product is 8-hydroxydeoxyguanosine. In some embodiments, the pterostilbene is administrated as a component of a nutraceutical formulation and may also contain superoxide dismutase, curcumin, alpha lipoic acid, piperine, and 2-dimethylaminoethanol. In some embodiments, the nutraceutical formulation is contained in capsules. In some embodiments, said capsules each contain about 200 mg pterostilbene and 806 mg of the combination of superoxide dismutase (200 mg), curcumin (212 mg), alpha lipoic acid (100 mg), piperine (10 mg), and 2-dimethylaminoethanol (124 mg). In some embodiments, a capsule is formulated including 100 mg pterostilbene and 423 mg of the combination of superoxide dismutase (100 mg), curcumin (106 mg), alpha lipoic acid (50 mg), piperine (5 mg), and 2-dimethylaminoethanol (62 mg). In some embodiments, the capsule further includes one or more binders, including, for example, magnesium stearate and fine rice flour.

In some embodiments is provided a method of alleviating or improving bone marrow suppression in an individual with cancer including: administering to an individual in need thereof a therapeutically effective amount of a pharmaceutical or nutraceutical composition consisting essentially of isolated or chemically-synthesized pterostilbene, its pharmaceutically or nutraceutically acceptable salts or isomers thereof and a pharmaceutically or nutraceutically acceptable carrier. In some embodiments, the composition is effective to decrease bone marrow suppression in said individual with cancer. In some embodiments, alleviating or improving bone marrow suppression is evaluated by performing complete blood counts (CBC) or bone marrow aspiration and biopsy. In some embodiments, pterostilbene is administered in a plurality of doses. In some embodiments, pterostilbene is administered as a component of a nutraceutical formulation. In some embodiments, the nutraceutical formulation also contains superoxide dismutase, curcumin, alpha lipoic acid, piperine, and 2-dimethylaminoethanol. In some embodiments, the nutraceutical formulation is contained in capsules. In some embodiments, the capsules each contain about 200 mg pterostilbene and 806 mg of the combination of superoxide dismutase (200 mg), curcumin (212 mg), alpha lipoic acid (100 mg), piperine (10 mg), and 2-dimethylaminoethanol (124 mg). In some embodiments, a capsule is formulated including 100 mg pterostilbene and 423 mg of the combination of superoxide dismutase (100 mg), curcumin (106 mg), alpha lipoic acid (50 mg), piperine (5 mg), and 2-dimethylaminoethanol (62 mg). In some embodiments, the capsule further includes one or more binders, including, for example, magnesium stearate and fine rice flour.

In some embodiments is provided a composition for augmenting anti-tumor immune responses in a cancer patient, said composition including a combination of ingredients consisting of pterostilbene, superoxide dismutase, curcumin, piperine, and 2-dimethylaminoethanol in a pharmaceutically acceptable carrier. In some embodiments, the composition is contained in capsules. In some embodiments, the capsules each contain about 200 mg pterostilbene and 806 mg of the combination of superoxide dismutase (200 mg), curcumin (212 mg), alpha lipoic acid (100 mg), piperine (10 mg), and 2-dimethylaminoethanol (124 mg). In some embodiments, a capsule is formulated including 100 mg pterostilbene and 423 mg of the combination of superoxide dismutase (100 mg), curcumin (106 mg), alpha lipoic acid (50 mg), piperine (5 mg), and 2-dimethylaminoethanol (62 mg). In some embodiments, the capsule further includes one or more binders, including, for example, magnesium stearate and fine rice flour. In some embodiments, the composition augments immune responses as determined by assessing the functions of immune cells. In some embodiments, the immune cells include, for example, B cells, T cells, innate lymphoid cells, natural killer cells, natural killer T cells, gamma delta T cells, macrophages, monocytes, dendritic cells, neutrophils, or myeloid derived suppressor cells, or combinations thereof.

As described herein B cells can be CD5+ B cells or CD5− B cells, and B cells can be naïve B cells or memory B cells.

T cells as described herein can be either CD4+ or CD8+ T cells, and can be CD28 positive T cells or CD28 negative T cells. T cells can also be either memory T cells or naïve T cells. Furthermore, T cells can be expressive of CD3. T cells can be regulatory cells. In some embodiments, T regulatory cells are expressive of proteins, including, for example CD25, CTLA-4, or FoxP3, or combinations thereof.

As described herein, Th1 cells are capable of secreting cytokines including, for example, interferon gamma, interleukin 2, and TNF-beta. In some embodiments, Th1 cells are expressive of markers, including, for example, CD4, CD94, CD119 (IFNγ R1), CD183 (CXCR3), CD186 (CXCR6), CD191 (CCR1), CD195 (CCR5), CD212 (IL-12Rβ1&2), CD254 (RANKL), CD278 (ICOS), IL-18R, MRP1, NOTCH3, or TIM3, or combinations thereof.

As described herein, Th2 cells are capable of secreting cytokines including, for example, IL-4, IL-5, IL-6, IL-9, IL-10, or IL-13, or combinations thereof. In some embodiments, Th2 cells express markers including, for example, CRTH2, CCR4, or CCR3, or combinations thereof.

As described herein, innate lymphoid cells can be innate lymphoid cells 1, innate lymphoid cells 2, innate lymphoid cells 3, or lymphoid tissue inducer cells, or combinations thereof. Innate lymphoid cell 1 are expressive of T bet and respond to IL-12 by secretion of interferon gamma but lack expression of CD56. Innate lymphoid cell 2 produce IL-4 and IL-13. Innate lymphoid cell 3 produce IL-17a and IL-22. Lymphoid tissue inducer cells are cells involved in the induction of memory T cells.

As described herein, macrophages include M1 or M2 macrophages. In some embodiments, M1 macrophages are capable of producing nitric oxide. In some embodiments, M2 macrophages are capable of producing arginase.

As described herein, dendritic cells can be myeloid dendritic cells or lymphoid dendritic cells. In some embodiments, myeloid dendritic cells are capable of stimulating Th1 immune responses in a mature state. In some embodiments, myeloid dendritic cells in said mature state express substantially higher levels of CD80 as compared to myeloid dendritic cells in an immature state. In some embodiments, myeloid dendritic cells in said mature state express substantially higher levels of CD86 as compared to myeloid dendritic cells in an immature state. In some embodiments, myeloid dendritic cells in said mature state express substantially higher levels of CD40 as compared to myeloid dendritic cells in an immature state. In some embodiments, lymphoid dendritic cells are capable of producing interferon alpha.

As described herein, dendritic cells can be myeloid dendritic cells or lymphoid dendritic cells. In some embodiments, myeloid dendritic cells are capable of stimulating Th1 immune responses in a mature state. In some embodiments, myeloid dendritic cells in said mature state express substantially higher levels of CD80 as compared to myeloid dendritic cells in an immature state. In some embodiments, myeloid dendritic cells in said mature state express substantially higher levels of CD86 as compared to myeloid dendritic cells in an immature state. In some embodiments, myeloid dendritic cells in said mature state express substantially higher levels of CD40 as compared to myeloid dendritic cells in an immature state. In some embodiments, lymphoid dendritic cells are capable of producing interferon alpha.

In some embodiments, assessment of an immune response of immune cells is performed by quantifying anticancer activities of said immune cells. In some embodiments, anticancer activities of the immune cells are assessed by determined the immune cells' ability to directly kill cancer cells, to induce other cells to kill cancer cells, to directly inhibit proliferation of cancer cells, to induce other cells to inhibit proliferation of cancer cells, to directly kill blood vessel cells associated with the cancer, to induce other immune cells to kill blood vessel cells associated with the cancer, to directly block proliferation of blood vessel cells associated with the cancer, or to induce other immune cells to block proliferation of blood vessel cells associated with the cancer.

In some embodiments, the immune responses are associated with enhanced production of Th1 cells, or with enhanced production of Th17 cells. In some embodiments, the anticancer immune responses are associated with enhanced production and/or lytic function of NK cells.

The preferred embodiments described herein are intended to illustrate the principles of the disclosure, but not to limit its scope. Other embodiments and variations to the preferred embodiments will be apparent to those skilled in the art and may be made without departing from the spirit and scope of the invention as defined in the claims.

EXAMPLES

Some aspects of the embodiments discussed above are disclosed in further detail in the following examples, which are not in any way intended to limit the scope of the present disclosure. Those in the art will appreciate that many other embodiments also fall within the scope of the invention, as it is described herein above and in the claims.

These Examples demonstrate the effectiveness of pterostilbene to induce de-repression of tumor targeting immune responses during treatment of cancer in a subject.
Experimental Materials and Methods The following experimental materials and methods were used for the Examples described below.

Example 1

Pharmaceutical Compositions Including Pterostilbene

The following example demonstrates an exemplary embodiment of a composition including pterostilbene.

A pterostilbene composition was prepared by combining the components provided in Table 1.

TABLE 1

| Component | Quantity |
| --- | --- |
| Pterostilbene | 100 mg |
| Curcumin | 106 mg |
| Superoxide Dismutase | 100 mg |
| Dimethylaminoethanol | 62 mg |
| Piperine | 5 mg |
| Alpha Lipoic Acid | 50 mg |
| Magnesium Stearate | 10 mg |
| Fine Rice Flour | 70 mg |

The ingredients were combined in a pharmaceutical composition. Magnesium stearate and fine rice flour were used as binders. Additional compositions including the composition as provided in Table 1, further including, for example, a chemotherapeutic agent, such as an anti-cancer antibody.

Example 2

Liposomal Pterostilbene

The following example demonstrates a method for the preparation of liposomal pterostilbene.

Pterostilbene is sparingly soluble in aqueous solution, making it difficult to incorporate into compositions. Pterostilbene is dissolved in deionized water at a maximum concentration by first dissolving pterostilbene in an organic solvent, such as ethanol, for example. This organic solvent containing pterostilbene is then diluted into deionized water to form a pterostilbene solution. The pterostilbene solution is mixed with lecithin. Lecithin is a phospholipid-containing substance, and the phospholipids are used to form liposomes. The mixture of pterostilbene and lecithin is homogenized in order to prevent the liposome-forming lipids from becoming inhomogeneous during liposome formation. The homogenized solution is mixed with flavors and stevia. An ultrasonic treatment is applied to the mixture, which results in the formation of liposomes containing pterostilbene. The liposomal pterostilbene is incorporated into the compositions described herein.

Example 3

Synergistic Inhibition of B16 Melanoma

The following example demonstrates that pterostilbene in combination with IL-2 synergistically inhibits B16 melanoma in mice.

Female C57BL/6 mice aged 8-12 weeks were purchased from The Jackson Laboratory. A murine melanoma cell line established from a C57BL/6 mouse and designated B16F10 was obtained from the American Type Culture Collection (ATCC) and was maintained in RPMI 1640 medium (Sigma-Aldrich) with 10% FBS, 1-glutamine, penicillin, and streptomycin at 37° C. in 5% $CO_2$. The cell line was cultured at 37° C. in a 5% incubator.

For induction of tumor growth, $5 \times 10^5$ B16 cells were injected subcutaneously into the hind limb flank. Tumor growth was assessed every 3 days by two measurements of perpendicular diameters by a caliper, and animals were sacrificed when tumors reached a size of 1 cm in any direction. Tumor volume was calculated by the following formula: (the shortest diameter$^2$×the longest diameter)/2. Mice treated represent 15 mice per group.

Animals were treated every second day with: Group A) Saline (diamonds—◇); B) pterostilbene; 25 µg/kg (squares—□), C) IL-2; 500 IU/mouse (triangles—Δ); and D) a combination of IL-2 and pterostilbene at the indicated concentrations (X). As shown in FIG. 1, tumor growth is inhibited by the administration of the combination of 25 µg/kg pterostilbene and 500 IU/mouse IL-2.

Example 4

Stimulation of Mitogen Induced IFN-Gamma Production by Pterostilbene

The following example demonstrates that pterostilbene alone or in combination with IL-2 stimulates IFN-gamma production in mice.

Figure 2:
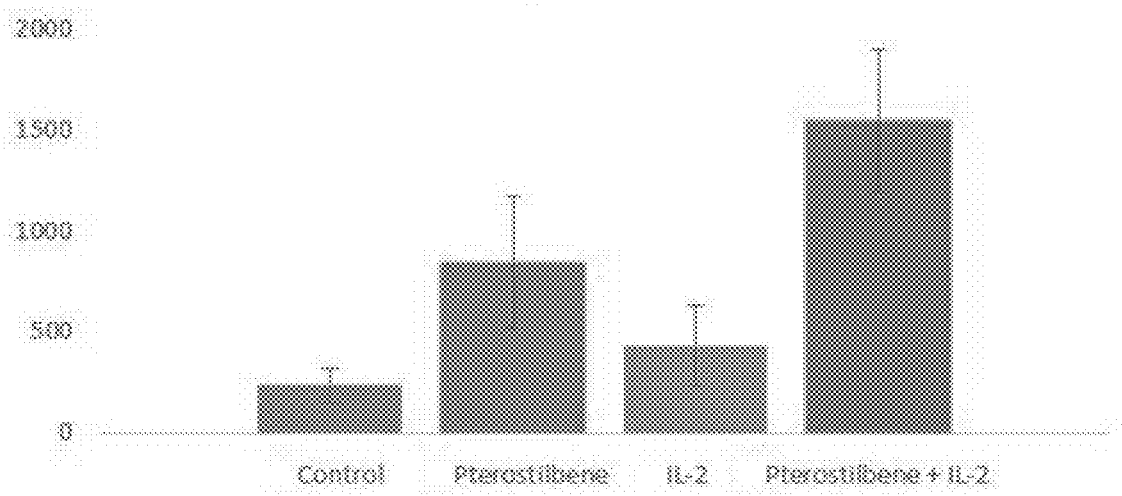
FIG. 2 illustrates the stimulation of mitogen induced IFN-gamma production by pterostilbene in mice. Mice were treated as described in FIG. 1 (from left to right: saline; 25 μg/kg pterostilbene; 500 IU/mouse IL-2; and a combination of IL-2 and pterostilbene at the indicated concentrations). Mononuclear cells were obtained and plated in 96-well plates and treated with Concanavalin A at 5 μg/mL. IFN-gamma was assessed by ELISA. The y-axis is expressed as ng/mL.

Mice from Example 3 where euthanized by cervical dislocation and spleens were excised in a sterile manner. Splenocyte mononuclear cells were obtained by hypotonic lysis and washed 3 times in PBS. Mononuclear cells were plated in 96 well plates and treated with Concanavalin A at 5 µg/mL. Interferon gamma was assessed by ELISA and expressed as ng/mL. As shown in FIG. 2, mononuclear cells of mice treated with saline (control) express about 200 ng/mL IFN-gamma. In contrast, mononuclear cells of mice treated with pterostilbene alone expressed about 900 ng/mL IFN-gamma, and mononuclear cells of mice treated with the combination of pterostilbene and IL-2 expressed about 1500 ng/mL IFN-gamma. As disclosed herein, enhanced expression of IFN-gamma elicits an immune response.

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

Although the instant disclosure sufficiently describes inventive aspects and embodiments, the numerous references cited herein may be of assistance in understanding the background and the state of the art. Accordingly, all of the publications cited herein are hereby incorporated by reference in their entireties into the present disclosure as if set forth in full herein.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method of treating cancer in a subject, comprising:
   selecting a subject having a cancerous tumor; and
   administering to the subject a composition comprising an effective amount of pterostilbene and IL-2.

2. The method of claim 1, wherein the effective amount of pterostilbene is 25 µg/kg and wherein the effective amount of IL-2 is 500 IU.

3. The method of claim 1, wherein the composition is administered orally or subcutaneously at least twice daily.

4. The method of claim 1 wherein the composition further comprises alpha lipoic acid.

5. The method of claim 1 wherein the composition further comprises superoxide dismutase (SOD).

6. The method of claim 1 wherein the composition further comprises 2-dimethylaminoethanol (DMAE).

7. The method of claim 1 wherein the composition further comprises piperine.

8. The method of claim 1 wherein the composition further comprises curcumin.

\* \* \* \* \*